(12) United States Patent
Polich

(10) Patent No.: US 10,799,465 B2
(45) Date of Patent: Oct. 13, 2020

(54) HOMEOPATHIC THERAPEUTIC METHOD AND COMPOSITIONS

(71) Applicant: Nancy Josephine Polich, Chicago, IL (US)

(72) Inventor: Nancy Josephine Polich, Chicago, IL (US)

(73) Assignee: Cearna, Inc., San Diego, CA (US)

( * ) Notice: Subject to any disclaimer, the term of this patent is extended or adjusted under 35 U.S.C. 154(b) by 0 days.

Patent file contains an affidavit/declaration under 37 CFR 1.130(b).

(21) Appl. No.: 16/000,955

(22) Filed: Jun. 6, 2018

(65) Prior Publication Data
US 2018/0280314 A1 Oct. 4, 2018

Related U.S. Application Data

(60) Continuation of application No. 15/130,447, filed on Apr. 15, 2016, now Pat. No. 10,022,335, which is a continuation-in-part of application No. 14/610,615, filed on Jan. 30, 2015, now abandoned, and a division of application No. 13/411,240, filed on Mar. 2, 2012, now abandoned.

(60) Provisional application No. 61/451,385, filed on Mar. 10, 2011, provisional application No. 61/448,913, filed on Mar. 3, 2011.

(51) Int. Cl.
A61K 9/70 (2006.01)
A61K 36/00 (2006.01)
A61K 31/00 (2006.01)
A61K 9/00 (2006.01)
A61K 36/28 (2006.01)
A61K 36/75 (2006.01)
A61K 36/45 (2006.01)
A61L 26/00 (2006.01)
A61K 41/00 (2020.01)
A61K 36/185 (2006.01)

(52) U.S. Cl.
CPC .......... A61K 9/7007 (2013.01); A61K 31/00 (2013.01); A61K 36/00 (2013.01); A61K 36/185 (2013.01); A61K 36/28 (2013.01); A61K 36/45 (2013.01); A61K 36/75 (2013.01); A61K 41/0004 (2013.01); A61L 26/008 (2013.01); A61L 26/009 (2013.01); A61L 26/0066 (2013.01); A61K 9/0014 (2013.01); A61L 2300/30 (2013.01); A61L 2300/412 (2013.01); A61L 2300/45 (2013.01); A61L 2300/606 (2013.01)

(58) Field of Classification Search
CPC .............................. A61K 9/7007; A61K 36/00
See application file for complete search history.

(56) References Cited

U.S. PATENT DOCUMENTS

| 4,646,730 A | 3/1987 | Schonfeld et al. |
| 5,162,037 A | 11/1992 | Whitson-Fischman |
| 5,429,590 A | 7/1995 | Saito et al. |
| 5,683,712 A | 11/1997 | Cavazza |
| 5,795,573 A | 8/1998 | Paradise |
| 6,013,679 A | 1/2000 | Kuo et al. |
| 6,024,734 A | 2/2000 | Brewitt |
| 6,447,813 B2 | 9/2002 | Davis |
| 6,471,971 B1 | 10/2002 | Wollenweber et al. |
| 6,486,213 B1 | 11/2002 | Chen et al. |
| 7,229,648 B2 | 6/2007 | Dreyer |
| 7,648,713 B2 | 1/2010 | Sawhney |
| 7,666,339 B2 | 2/2010 | Chaouk et al. |
| 7,923,040 B2 | 4/2011 | Dreyer |
| 2002/0013300 A1 | 1/2002 | Capelli-Schellpfeffer |
| 2003/0003140 A1 | 1/2003 | Domb et al. |
| 2004/0019107 A1 | 1/2004 | Taub et al. |
| 2004/0109895 A1 | 6/2004 | Hensley |
| 2004/0180101 A1* | 9/2004 | Dreyer ..................... A61K 9/06 424/725 |
| 2004/0242770 A1 | 12/2004 | Feldstein et al. |
| 2005/0136122 A1 | 6/2005 | Sadozai et al. |
| 2005/0191270 A1 | 9/2005 | Gruening et al. |
| 2005/0238693 A1 | 10/2005 | Whyte |
| 2006/0161097 A1 | 7/2006 | Domb |
| 2006/0182787 A1 | 8/2006 | Jaenichen et al. |
| 2007/0065396 A1 | 3/2007 | Morariu |
| 2007/0110676 A1 | 5/2007 | Clymer et al. |
| 2007/0154527 A1 | 7/2007 | Myers et al. |
| 2007/0212406 A1 | 9/2007 | Taub et al. |

(Continued)

FOREIGN PATENT DOCUMENTS

| CN | 101107003 | 1/2008 |
| EP | 1327442 | 7/2003 |

(Continued)

OTHER PUBLICATIONS

"Aquamed Technologies, Inc.," http://www.aguamedinc.net/, accessed Jan. 12, 2012.

(Continued)

Primary Examiner — Amy L Clark

(74) Attorney, Agent, or Firm — Baker Botts L.L.P.

(57) ABSTRACT

Methods of producing a Hydrophilic Homeopathic Aqueous Substance Active (HASA)-gel matrix, include the steps of: (a) combining a homeopathic compound and an uninhibited aqueous composition to produce a HASA; (b) combining the HASA with at least one hydrophilic gelling agent; and (c) thereafter, forming the hydrophilic HASA-gel matrix by use of at least one of a thickening agent, a crosslinking agent, or a polymerization agent.

19 Claims, No Drawings

(56) References Cited

U.S. PATENT DOCUMENTS

| | | |
|---|---|---|
| 2007/0275096 A1 | 11/2007 | Banks |
| 2007/0275098 A1 | 11/2007 | Banks |
| 2008/0038306 A1 | 2/2008 | David |
| 2008/0193576 A1 | 8/2008 | Lombardo et al. |
| 2008/0279902 A1 | 11/2008 | Luria et al. |
| 2008/0312572 A1 | 12/2008 | Riesinger |
| 2009/0104292 A1 | 4/2009 | Alam |
| 2009/0191278 A1 | 7/2009 | Rajesh |
| 2009/0214628 A1 | 8/2009 | deRijk |
| 2009/0232904 A1 | 9/2009 | Quinto et al. |
| 2009/0270310 A1 | 10/2009 | Whyte |
| 2010/0124549 A1 | 5/2010 | Studin |
| 2010/0124568 A1 | 5/2010 | Eramo et al. |
| 2010/0135935 A1 | 6/2010 | Leshchiner et al. |
| 2010/0151052 A1 | 6/2010 | Wycoff |
| 2010/0221332 A1 | 9/2010 | Banks |
| 2010/0226863 A1 | 9/2010 | Piraino |
| 2010/0239569 A1 | 9/2010 | Epshtein |
| 2010/0316737 A1 | 12/2010 | Barrington et al. |
| 2011/0028412 A1 | 2/2011 | Cappello et al. |
| 2011/0038949 A1 | 2/2011 | Oswal et al. |
| 2011/0135747 A1 | 6/2011 | Polich |
| 2011/0206774 A1 | 8/2011 | Manickam |
| 2011/0244039 A1 | 10/2011 | Domb et al. |

FOREIGN PATENT DOCUMENTS

| | | |
|---|---|---|
| JP | 2000-297009 | 10/2000 |
| JP | 2002-020273 | 1/2002 |
| JP | 2005-160890 | 6/2005 |
| WO | WO 2002/032405 | 4/2002 |
| WO | WO 2004/010952 | 2/2004 |
| WO | WO 2004/073794 | 9/2004 |
| WO | WO 2004/082597 | 9/2004 |
| WO | WO 2006/135493 | 12/2006 |
| WO | WO 2008/019498 | 2/2008 |
| WO | WO 2010/025430 | 3/2010 |

OTHER PUBLICATIONS

"Arch Facial Plast Surg—Effect of Homeopathic Arnica Montana on Bruising in Face-Lifts: Results of . . .," http://archfaci.ama-assn.org/cgi/content/full/8/1/54, accessed Apr. 27, 2009.

"Arnica—say goodbye to bruises," http://www.ivillage.co.uk/print, accessed Apr. 27, 2009.

"Brauer Arnica Sports Bruising Gel Relief 100," httg://www.getgrice.com.au/Brauer-Arnica-Sport-Bruising-Gel-relief-100-Gpnc_321-33081574.htm, accepted Apr. 27, 2009.

Generic Name: Arnica (Arnica Montana)—Topical, http://www.medicinenet.com/arnica_arnica montana-topical/article.htm, accessed Apr. 27, 2009.

"Homeopathic Medicine: An Overview with Specific Applications for the Orthopaedic Patent," Techniques in Orthopaedics, vol. 18(1):54-61 (2003), http://journals.lww.com/techortho/Abstract/2003/03000/Homeopathic_Medicine_An_Overview, accessed Apr. 27, 2009.

"Homeopathy—Introduction and brief history," http://new.hungarovet.com/eng/homeopathyintrouction-and-brief-history/, accessed Apr. 27, 2009.

"Homeopathy for Health," Product: Arnica Oil 1 oz. and 20 oz., http://www.elixirs.com/products.frm?productcode=HY201, accessed Apr. 27, 2009.

"Homoeopathy," http://www.irishwolfhounds.org/homeopathy.htm, accessed Apr. 27, 2009.

"Injurease Cream with Arnica," http://www.naturalhealthorganices.com/au/lnlurease-Creamwith-Arnica-Qr-2354.html, accessed Jun. 17, 2009.

"Injurease with Arnica," http://www.vivekahealth.com.au/injurease.html, accessed Jun. 17, 2009.

"Things to Know about Arnica Montana Dosage," http://www.nutritional-supplements-Health-guide.com/arnica-montana-dosage.html, accessed Apr. 27, 2009.

"Unravelling the confusion around arnica's herbal and homoeopathic use," The Pharm. Journ., vol. 275, 289-290, www.pjonline.com, 2005.

Barrett, "Homeopathy: The Ultimate Fake," Retrieved from the Internet on Jun. 26, 2016. Retrieved from: <URL: http://www.quackwatch.com/01/QuackelyRelatedTopics/Homeo.hml>, Internet date: Aug. 1999.

Bates, "Arnica's bruised reputation," J. Pharm., vol. 270, p. 330, Mar. 2003.

Chinese Office Action to Chinese Patent Application No. 201280011603.0, 8 pages, received Mar. 2, 2016.

DeLivera, "ACL Injury," http://www.homepathyandmore.com/forum/viewtopic.php?t=1300>, posting date: Sep. 5, 2007.

European Office Action to Application No. 12752964.2 dated Oct. 27, 2016.

European Search Report received in Application No. 12752964.2, dated Mar. 12, 2015.

Hahnemann's Organon of Medicine,§ 204 Fifth Edition,§ 205 Fifth Edition, http://www.homeopathyhome.com/reference/organon/organon.html, Jan. 19, 2011.

Hennink et al., "Novel crosslinking methods to design hydrogels," Advanced Drug Delivery Reviews, 54:13-36, 2002.

International Preliminary Report and Written Opinion received in related PCT Application No. PCT/US2012/027546 dated Feb. 13, 2014.

International Search Report and Written Opinion dated Jun. 12, 2012 in PCT Application No. PCT/US2012/027546.

Kalia et al., "Domains formation mediated by electromagnetic fields in very dilute aqueous solutions: 2. Quantum electrodynamic analyses of experimental data on strong electrolyte solutions," Water, 7 :48-69, Oct. 27, 2015.

Karow et al., "Efficacy of Arnca Montana D4 for healing of wounds after HalluX valgus surgery compared to diclofenac," J. Altern Complement Med., 14(1): 17-25, 2008.

Kaziro et al., "Metronidazole (flagyl) and Arnica Montana in the Prevention of Post-Surgical Complications, a Comparative Placebo Controlled Clinical Trial," British J. of Oral and MaXillofacial Surgery, vol. 22(1):42-49 (Feb. 1984), http://www.sciencedirect.com/science?ob=ArticleURL&_udi=B6WC5-4C892YG-24&_user=10&r, accessed Apr. 27, 2009.

Knoble Yoshida & Dunleavy LLC, Patentability Report, dated Jul. 7, 2010.

Konovalov et al., "Reviews: Formation of Nanoassociates as a key to understanding of physicochemical and biological properties of highly dilute aqueous solutions," Russ. Chen. Bull, Int. Ed, 63(1):1-14, Jan. 2014.

Office Action dated Mar. 14, 2012 received in related Chinese Application No. 200981043723.4.

Office Action received for Australian Application No. 2012223195, 5 pages, dated May 2, 2016.

Office Action received for Chinese Application No. 201280011603, 8 pages, dated Dec. 21, 2015.

Office Action received for Japanese Application No. 2013-556651 with English Translation, 8 pages, dated Sep. 30, 2016.

Office Communication issued in U.S. Appl. No. 13/411,240, dated Jan. 7, 2014.

Office Communication issued in U.S. Appl. No. 13/411,240, dated May 29, 2013.

Office Communication issued in U.S. Appl. No. 13/411,240, dated Apr. 4, 2013.

Office Communication issued in U.S. Appl. No. 14/610,615, dated May 1, 2017.

Office Communication issued in U.S. Appl. No. 14/610,615, dated Oct. 20, 2016.

Office Communication issued in U.S. Appl. No. 15/130,447, dated Jul. 19, 2017.

Office Communication issued in U.S. Appl. No. 15/130,447, dated May 9, 2017.

Office Communication issued in U.S. Appl. No. 15/130,447, dated Jul. 19, 2016.

Patent Examination Report No. 1 dated Jun. 13, 2012 in related Australian Application No. 2009285556.

(56) References Cited

OTHER PUBLICATIONS

Polich, J., Chiropractor Presentation, Homeopathy for the Chiropractor, Lecture 2, Jul. 20, 2006.
Polich, J., DC Tracts Presentation Addendum, Spring 2006.
Polich, J., INJUREASE® "The 1st Solution for Musculoskeletal Injuries," *DuPage Homeopathic* Center, 2005.
Polich, J., Transcript of DC Tracts Presentation (training documents), Spring 2006.
Schmidt, "Same laws of science apply to all medical practices—if only people realized that," *J. Pharm.*, vol. 270, p. 398, Mar. 2003.
Schneider et al., "A homeopathic ointment preparation compared with 1% diclofenac gel for acute symptomatic treatment of tendinopathy," *Explore*, 1(6):446-452, 2005.
Second Office Action issued in Chinese Patent Application No. 200980143723.4 dated Jan. 10, 2003.
Second Office Action issued in Chinese Patent Application No. 201280011603.0, 10 pages, dated Sep. 26, 2016.
Supplementary European Search Report dated Oct. 16, 2012 in related European Patent Application No. EP 09 81 0701.
Tranoudis, et al., "Water properties of soft contact lens materials," Eurolens Research, Department of Optometry, The University of Manchester, *Contact Lens & Anterior Eye*, 27:193-208, (2004).
Whitaker, "If we endorse quack cures we really deserve to be dubbed 'Baddy Chemists'" *J. Pharm.*, vol. 268, p. 288, Mar. 2002.
Bergamante et al., "Effect of vehicles on topical application of aloe vera and arnica montana components," *Drug Delivery*, 14:427-432, 2007.
Office Communication issued in European Patent Application No. 12752964.2, dated Feb. 5, 2019.

\* cited by examiner

HOMEOPATHIC THERAPEUTIC METHOD AND COMPOSITIONS

RELATED APPLICATIONS

The present application is a continuation of U.S. application Ser. No. 15/130,447, filed Apr. 15, 2016, which is a continuation-in-part of U.S. application Ser. No. 14/610,615, filed Jan. 30, 2015, now abandoned, which is a divisional application of U.S. application Ser. No. 13/411,240, filed Mar. 2, 2012, now abandoned, which claims the benefit of priority to U.S. Provisional Application Ser. No. 61/448,913, filed Mar. 3, 2011 and U.S. Provisional Application Ser. No. 61/451,385, filed Mar. 10, 2011, each of which is incorporated herein in its entirety by reference.

FIELD OF THE INVENTION

The present invention relates to compositions comprising a therapeutically effective amount of a homeopathic aqueous substance active (HASA) and at least one hydrophilic gelling agent, as well as methods of producing and applying the HASA and hydrophilic HASA-gel matrix.

BACKGROUND OF THE INVENTION

Homeopathy is a medical practice that treats a disease, affliction or condition by administering small amounts of a natural substance. A fundamental aspect of homeopathy is the stimulation of the body's natural healing process by administering a homeopathic remedy capable of producing the same or similar symptoms for which treatment is sought in a healthy individual. For example, *arnica*, which causes bruising in a healthy individual when administered in concentrated dosages, is a common homeopathic remedy for treating bruising.

In the United States, the preparation and sale of homeopathic remedies are regulated by the Homeopathic Pharmacopoeia of the United States (HPUS). According to HPUS guidelines, homeopathic remedies are prepared by successively diluting herbals and other natural substances in a water and/or alcohol solution. Because homeopathic potency is inversely related to concentration, the greater the dilution the higher the potency of the homeopathic remedy.

The most common methods for administering homeopathic remedies involve sipping a water based solution or orally dissolving a homeopathic compound infused sucrose/lactose pellet in the mouth. Certain orally administered homeopathic remedies may be formulated as medium to high compositions to enhance therapeutic effectiveness. While these oral administrations are effective for treating certain systemic diseases, they may not be effective for treating some localized ailments. This may be because oral formulations cannot be directly administered to location of ailment; the administration area is limited; and therapy is likely limited to less than about 20 minutes due to the natural cleansing process of the mouth for a typical number 40 pellet.

Another common method of administering homeopathic remedies involves topical administration. Typically, topical gel and cream based homeopathic remedies may be directly administered to the site of an ailment or injury. These remedies typically include low potencies of homeopathic agents, and are formulated as gels, lotions and creams.

U.S. Pat. No. 7,229,648 (Dreyer) discusses homeopathic gel formulations for treating pain and inflammation having a potency of greater than 30 C, such as 30 C, 200 C, 1M, 10M and 50M. Specifically, Dreyer discusses mixing a homeopathic composition with a gel base. For example, Dreyer discusses combining 8% of homeopathic remedies into 92% gel base. Additionally, Dreyer teaches that its topical gel formulation should be dry to the touch within a few minutes of application.

U.S. Patent Application Publication No. 2008/279902 (Luria) discloses a cosmetic composition including a homeopathic complex that may be formulated as a transdermal or topical paste, cream, lotion, ointment or gel having a potency of about 1×. to about 50,000 Q or about 100 C to about 50,000 Q.

Although numerous homeopathic formulations are commercially available, there still remains a need to develop effective medium to high potency formulations that when topically administered, may be particularly suitable for preventing or treating severe ailments and injuries.

SUMMARY OF THE INVENTION

In one embodiment, the present invention relates to a method of producing a hydrophilic homeopathic aqueous substance active (HASA)-gel matrix. The method includes (a) combining a homeopathic compound and an uninhibited aqueous composition to produce a HASA; (b) combining the HASA with at least one hydrophilic gelling agent; and (c) thereafter, forming the hydrophilic HASA-gel matrix by use of at least one of a thickening agent, a crosslinking agent, or a polymerization agent. In certain embodiments of the method, the homeopathic compound may include a potency of at least 6×, at least 6 C, at least 30 C, at least 400 C, at least 1M, or at least 10M, or alternatively, the compound may be diluted to a factor of at least $10^{-4}$, $10^{-6}$, $10^{-8}$, $10^{-10}$, $10^{-12}$, $10^{-20}$, 1060, $10^{-100}$, $10^{-200}$, $10^{-400}$, $10^{-600}$, $10^{-1000}$, $10^{-10000}$, $10^{-100000}$, $10^{-10000000}$, $10^{-100,000,000}$, or $10^{-100,000,000}$ for example. It is understood that the dilutions are examples only and that any dilution factor within that range of from $10^{-4}$ to $10^{-100000000}$ is also contemplated by this disclosure. The matrix may be in the form of a sheet. At least one external layer may be affixed to a first major surface of the gel sheet. A permeable layer may be affixed to a second major surface of the gel sheet opposite the first major surface. Alternatively, the hydrophilic HASA-gel matrix may be in a flowable form.

In another embodiment, the present invention relates to a method for preventing or reducing tissue damage comprising contacting the hydrophilic HASA-gel matrix produced by the method, including the steps of (a) combining a homeopathic compound and an uninhibited aqueous composition to produce a HASA; (b) combining the HASA with at least one hydrophilic gelling agent; and (c) thereafter, forming the hydrophilic HASA-gel matrix by use of at least one of a thickening agent, a crosslinking agent, or a polymerization agent, with a biological tissue of an animal in need of such prevention or reduction, wherein the homeopathic compound has a potency of at least 6× or a dilution factor of at least $10^{-4}$. In the method, the tissue damage may be the result of a surgical procedure. In the method, the hydrophilic HASA-gel matrix composition may be contacted with the biological tissue from about 1 minute to about 72 hours prior to the occurrence of tissue damage. In the method, the hydrophilic HASA-gel matrix may be in contact with the biological tissue for duration of about 1 minute to about 48 hours.

In another embodiment, the present invention relates to a method of treating ligament damage in a patient's knee comprising contacting the hydrophilic HASA-gel matrix produced by the method, including (a) combining a homeopathic compound and an uninhibited aqueous composition to produce a HASA; (b) combining the HASA with at least one hydrophilic gelling agent; and (c) thereafter, forming the hydrophilic HASA-gel matrix by use of at least one of a thickening agent, a crosslinking agent, or a polymerization agent, with the knee, wherein the homeopathic compound has a potency of at least 6x or a dilution factor of at least $10^{-4}$, and wherein no surgical procedures are required to repair the ligament damage. The method further includes having the patient wear a straight leg brace to prevent bending.

In yet another embodiment, the present invention relates to an intermediate composition for making a hydrophilic homeopathic aqueous substance active (HASA)-gel composition. The intermediate composition comprises a therapeutically effective amount of a HASA combined with at least one hydrophilic gelling agent before the gel is formed. The HASA comprises a homeopathic compound at has a potency of at least 6x or a dilution factor of at least $10^{-4}$ and an uninhibited aqueous composition. The homeopathic compound may have a potency of at least 400 C, a potency of at least 1M, or a potency of at least 10M.

In yet a further embodiment, the present invention relates to a homeopathic agent delivery device that includes a sheet of a porous hydrophilic polymer and HASA within the sheet, wherein the HASA comprises a homeopathic compound that has a potency of at least 6x or a dilution factor of at least $10^{-4}$ and an uninhibited aqueous composition.

In yet another embodiment, the present invention relates to a method for preventing or reducing tissue damage. The method includes contacting a biological tissue of an animal in need of such prevention or reduction with the delivery device that includes a sheet of a porous hydrophilic polymer and HASA within the sheet, wherein the HASA comprises a homeopathic compound that has a potency of at least 6x or a dilution factor of at least $10^{-4}$ and an uninhibited aqueous composition. The tissue damage may be the result of a surgical procedure. In the method, the homeopathic agent delivery device may be contacted with the biological tissue from about 1 minute to about 72 hours prior to the occurrence of tissue damage. In the method, the homeopathic agent delivery device may be in contact with the biological tissue for duration of about 1 minute to about 48 hours.

In yet another embodiment, the present invention relates to a method of treating ligament damage in a patient's knee comprising the knee with the delivery device that includes a sheet of a porous hydrophilic polymer and HASA within the sheet, wherein the HASA comprises a homeopathic compound that has a potency of at least 6x or a dilution factor of at least $10^{-4}$ and an uninhibited aqueous composition, and wherein no surgical procedures are required to repair the ligament damage. The method may further include having the patient wear a straight leg brace to prevent bending.

In yet further embodiment, the present invention relates to a method of verifying that a homeopathic agent delivery device is therapeutically effective comprising the steps of: (a) bruising a person; (b) applying the delivery device that includes a sheet of a porous hydrophilic polymer and HASA within the sheet, wherein the HASA comprises a homeopathic compound that has a potency of at least 6x or a dilution factor of at least $10^{-4}$ and an uninhibited aqueous composition; and (c) comparing the results to a control.

In yet another embodiment, the present invention relates to a hydrophilic HASA-gel matrix comprising at least 31% at least 41% or at least 50% of a homeopathic aqueous substance active (HASA), and at least one hydrophilic polymer, forming a gel, wherein the HASA comprises a homeopathic compound that has a potency of at least 6x or a dilution factor of at least $10^{-4}$ and an uninhibited aqueous composition.

In each of these embodiments, the homeopathic compound includes at least one of *Arnica Montana, Bellis perennis, Calcarea phosphorica, Calendula, Hypericum perforatum, Ledum palustre, Rhus toxicodendron, Millefolium, Ruta graveolens, Symphytum officinale, Apis Mel, Cantharis, Urticartia Urens, Belladonna, Ferrum Metallicum, Staphasagria, Hepar Sulphuricum, Euphatorium perfoliatum, Bryonia, Naturm Sulphuricum, Calcarea carbonica,* and *Hamamelis.*

DETAILED DESCRIPTION

For illustrative purposes, the principles of the present invention are described by referencing various embodiments thereof. Although certain embodiments of the invention are specifically described herein, one of ordinary skill in the art will readily recognize that the same principles are equally applicable to, and can be employed in other compositions and methods. Before explaining the disclosed embodiments of the present or present invention in detail, it is to be understood that the invention is not limited in its application to the details of any particular embodiment shown. The terminology used herein is for the purpose of description and not of limitation.

As used herein, the term "homeopathic compound" refers to a composition formulated from one or more naturally derived substances, such as herbs, that have been diluted. In one embodiment, the composition may be prepared according to the Homeopathic Pharmacopoeia of the United States (HPUS) standards and procedures, wherein the natural substance is serially diluted and sufficiently succussed to achieve a desired potency using conventional homeopathic potentization methods. Over the years, many variations of the art of homeopathic production have been employed, including varying the succussion to ratio as in the Dunham potencies and using water to succuss the homeopathic compound as in the Finke remedies. In some cases succussion is not even employed. For purposes of the present invention, the homeopathic remedies may be formulated according to methods not taught in the HPUS, which may involve the preparation of tinctures, dilutions, infusions, water or alcohol extracts, powdered plasters, decoctions, poultices, or any other methods of preparations.

As used herein, the term "potency" is defined according to the HPUS and may be quantified according to various scales, such as the decimal X scale, centesimal C scale and quintamillesimal Q scale. In general, a decimal X scale dilution is half the value of a C scale dilution, and a given dilution on the Q scale is about 2.35 times the value of a C scale dilution. For example, a 1:10 dilution has a potency of 1 decimal (1x), which is equal to a concentration of $10^{-1}$. Similarly, a 1:100 dilution has a potency of 1 centesimal (1 C), which may be expressed as a potency of 1 C or a concentration of $10^{-200}$, and a dilution 1:1000 dilution has a potency of 1 millesimal (1M) or a concentration of $10^{-2000}$. For purposes of the present invention, a homeopathic compound having a $10^{-60}$ concentration is equivalent to a potency of 30 C or 60x, a homeopathic compound having a $10^{-400}$ concentration is equivalent to a potency of 200 C or 400x, a concentration of $10^{-7000}$ concentration is equivalent to a potency of 500 C, a concentration of $10^{-2000}$ is equivalent to a potency of 1000 C or 1M, a concentration $10^{-5,000}$ is equivalent to a potency of 2.5M, a concentration of $10^{-10,000}$ is equivalent to a potency of 5M, a concentration of $10^{-20,000}$ is equivalent to a potency of 10M, a concentration of $10^{-50,000}$ is equivalent to a potency of 25M, a concentration of $10^{-100,000}$ is equivalent to a potency of 50M, a concentration of $10^{-200,000}$ is equivalent to a potency of 100M, a concentration of $10^{-500,000}$ is equivalent to a potency of 250M, a concentration of $10^{1,000,000}$ is equivalent to a potency of 500M, a concentration of $10^{-2,000,000}$ is equivalent to a potency of 1 CM, a concentration of $10^{-5,000,000}$ is equivalent to a potency of 2.5 CM, a concentration of $10^{-1,000,000}$ is equivalent to a potency of 5 CM, and a concentration of $10^{-20,000,000}$ is equivalent to a potency of 10 CM. Homeopathic remedies may also be formulated using the LM scale, including 1 LM, 2 LM and upwards or 50,0000 Q and upwards. Varying the amount of sucussing may or may not affect the therapeutic activity.

Therapeutic effect is not determined in the same way as herbals or pharmaceuticals. In general, homeopathic remedies are made in low concentrations, typically, well below the level where the molecular concentration of the active ingredient is important. As evidenced in the above examples, potency is inversely related to concentration; consequently, the greater the dilution, the higher the potency of a homeopathic compound. A desired potency may be achieved by making repeated dilutions of a homeopathic compound. For instance, an active drug having a potency of 1 C may be prepared by making a 1 in 100 dilution of an active drug or a tincture, extract or derivative thereof (for example, 1 ml of a tincture can be mixed with 99 ml of a diluent liquid and then succussed at least 10 times according to known potentization procedures in homeopathy). A potency of 2 C may be prepared by making a 1:100 dilution of an active drug having a potency of 1 C and then succussing at least 10 times. A potency of 3 C may be prepared by making a 1:100 dilution of an active drug having a 2 C potency and then succussing at least 10 times. Where a homeopathic compound includes a combination of ingredients, the designated potency of the composition is the same potency for each individual ingredient. For example, a 10M *Arnica* and *Ledum* homeopathic compound indicates that a 10M potency of *Arnica* and a 10M potency of *Ledum*.

As used herein dilution factor and diluton to a certain ratio are used interchangeably and are meant to convey their normal meaning in the art. For example, a dilution of 1 gm or 1 ml of solute into 99 ml of solvent is a dilution ratio of 1:100 or a dilution factor of $10^{-2}$. For dilute solutions such as described herein, it is common to perform a serial dilution. Continuing with the example, removing 1 ml from the $10^{-2}$ solution and adding that ml to 99 ml of solvent results in a dilution ratio of 1:10000 or a dilution factor of $10^{-4}$. Repeating those steps would produce dilution factors of $10^{-6}$, $10^{-8}$ etc.

Unless otherwise indicated all percentages are to be read as percentages by weight.

As used herein, the term "injury" refers to any bodily damage, wound, condition thereof, or any associated symptoms thereof.

For purposes of the present invention, the term "ailment," as used herein, refers to any disease, disorder, associated condition thereof, or associated symptom thereof.

As used herein, the term "natural substances" refers to any material that may be obtained from nature, including but not limited to plant or mineral extracts, such as powder extracts or fluids extracts, one or more active compound of an animal, plant or mineral, any parts of an animal, plant or mineral, or a whole plant or mineral, tinctures thereof, and mixtures thereof.

As used herein, the term "treatment" or "treating" refers to any means for producing a beneficial result in a vertebrate (such as a subject, patient or individual) affected with an ailment or suffering from an injury, including but not limited to, substantially preventing, substantially reducing the severity of, substantially improving the condition of, substantially expediting the healing of or substantially curing an ailment, an injury, one or more one symptoms, conditions or aspects thereof, or combinations thereof.

As used herein, the term "topical" application or administration refers to the direct administration of a composition onto one or more bodily surfaces, such as any epithelial tissue, including, but not limited to, skin; mucosa; connective tissue, including cartilage and bone; muscles; and nervous tissue; organs; nerves; brain; arteriol; lymphatic or combinations thereof. In one embodiment, topical application refers to administration of a composition to the skin or mucous membranes including but not limited to the vagina, anus, throat, eyes and ears. Unless otherwise stated or implied, topical applications or administrations include transdermal administrations.

As used herein, the term "uninhibited aqueous composition," refers to an aqueous medium containing water molecules such that the water molecules are free to move, bind and/or clump, and are not impacted by any substances or forces which restrict the natural movement of individual or groups of water molecules. In addition, it should have properties found in naturally occurring water such as that in a sample taken from Lake Michigan 1 mile or more from the shore at any location. The comparative test is an example of at least one test that can be used to determine whether or not HASA does or does not form. A substance is considered to be an uninhibited aqueous composition when said substance, after being combined with a homeopathic compound produces a composition that performs similarly to the control test mixture for the comparative test, demonstrating a significant improvement in the treatment of tissue damage, when compared to placebo. Such a significant improvement can be demonstrated, by example, by a statistical significance (such as p less than 0.1, p less than 0.5, etc.). Examples of an "uninhibited aqueous composition" include, but are not limited to, pure water, fresh water, hard water, soft water, brackish water, seawater, distilled/demineralized water, boiled water, raw water, rain water, snow water, filtered water, reverse osmosis, de-ionized water, steam condensate, boiler feed water, potable water, cooling water, waste water, process or hydrotest water/firewater, artesian water/artesian well water, fluoridated water, mineral water, purified water, sparkling water, spring water, sterile/sterilized water, well water, utility water, drinking water, softened water, municipal/tap water, soda water, seltzer water, tonic water, laboratory water types 1, 2, and 3, non-potable, potable (drinkable) water, USP purified water, USP water for injection (WFI), USP sterile water for injection, USP sterile water for inhalation, USP bacteriostatic water for injection, USP sterile water for irrigation, and combinations thereof. Deionized (DI) water may also be used. Organizations such as Clinical and Laboratory Standards Institute (CLSI) and the American Society for Testing and Materials (ASTM) categorize DI water into types I-III and I-IV, respectively, based upon the degree of purity.

As used herein, the term "homeopathic aqueous substance active" or "HASA" is defined as a therapeutically effective combination of an uninhibited aqueous composition and at least one homeopathic compound. A HASA can be identified in certain embodiments as a solution that includes nanoassociates as described in Konovalov et al., (2014). Reviews: Formation of nanoassociates as a key to understanding of physicochemical and biological properties of highly dilute aqueous solutions. Russ Chem Bull Int Ed 63: 1-14. (Incorporated herein in its entirety by reference)

The term "therapeutically effective amount" of a homeopathic agent as used herein, is an amount that is effective for the prevention and/or treatment of an ailment or injury in a mammal (preferably a human), without undue adverse side effects (such as toxicity, irritation, or allergic response), commensurate with a reasonable benefit/risk ratio when used in the manner of this invention. The specific "therapeutically effective amount" will vary with factors, such as the particular condition being treated, the physical condition of the treated mammal, the size and weight of the treated mammal, the duration of treatment, the nature of concurrent therapy (if any), the specific dosage form to be used, other components present in a given dosed composition, and the dosage regimen desired for the component or composition. For example, a therapeutically effective amount of HASA may be the amount of HASA that is capable of reducing bruising in a treated subject as compared to the control or untreated subject. Additionally, a comparative test is one example of assessing the therapeutic effect of the HASA.

As used herein, the term "inert excipient" refers to a physiologically acceptable carrier or excipient that does not interfere with the effectiveness of HASA.

The term "hydrophilic gelling agent" refers to any hydrophilic substance that is transformed into a hydrophilic gel following the application of at least one of a thickening agent, a crosslinking agent, or a polymerization agent.

The term "gel" refers to a semi-solid substance that comprises a gelling agent to provide viscosity or stiffness. Preferably, the gel of the present invention is formed upon the use of at least one of a thickening agent, crosslinking agent or a polymerization agent, and does not flow at room temperature. The gel includes any one of a hydrogel, a cream, an ointment, a salve, a balm, a lotion, a liniment, a cream gel, a lotion ointment, a decoction, or a combination thereof. Gels may also include emulsions (e.g., oil in water emulsions and water in oil emulsions).

The gel may comprise a cross-linked structure or a non-cross-linked structure. Preferably, the gelling agents are hydrophilic polymers that are cross-linked to form the gel. Preferably, the cross-linked hydrophilic polymers are subjected to a low-energy process for crosslinking the hydrophilic polymers either prior to, during, or after the hydrophilic gelling agents have been combined with the HASA, or combinations thereof. In addition, the hydrophilic polymers may be cross-linked by the addition of a suitable base (e.g., NaOH, KOH, triethanolamine) to form a gel.

There are various types of gels and include silica gel, silicone gel, aloe vera gel, agarose gel, nafion, polyurethane, elastomers (thermoplastic, mineral-oil thermoplastic, etc.), ion-exchange beads, organogels, xerogels and hydrocolloids.

Suitable examples of hydrophilic gelling agents include, but are not limited to, cationic, anionic, or nonionic polar polymers.

Examples of polar polymers include, but are not limited to polyethylene oxide, polypropylene oxide, polyacrylamide, polyvinyl alcohol, polyvinylpyrollidone, polyacrylonitrile, and their co-polymers.

Examples of anionic polymers include, but are not limited to polyacrylic acid, polysulfonic acid, and their salts.

Generally, hydrophilic gelling agents contain polar or charged functional groups. Examples of hydrophilic gelling agents, grouped by the chemistry of their structure, are acrylics, amine-functional polymers, ethers, styrenes: polystyrenesulfonate and related polymers, vinyl acids, vinyl alcohols, and polyvinyl pyrrolidone. Acrylics include acrylamides, acrylates: poly(acrylic acid) and related polymers, maleic anhydride copolymers, methacrylate, ethacrylate and related polymers.

The hydrophilic gelling agents may further include synthetic and natural polymers. Examples of synthetic polymers include, but are not limited to alkali metal salts of polyacrylic acids, polyacrylamides, polyvinyl alcohol, polyacrylates, polyacrylamides, polyvinyl pyridines, poly(vinyl alcohol) or polyion complexes, hydrolyzed acrylonitrile grafted starch, acrylic acid grafted starch, and isobutylene maleic anhydride copolymers, and the like, and mixtures thereof. Suitable examples of natural polymers include, but are not limited to polysaccharides, carboxymethylcellulose, hyaluronic acid, dextran, dextran sulfate, heparin, chondroitin sulfate and proteins, such as gelatin, collagen, and albumin, cellulose, starch, chitin and chitosans, lignins, various polysaccharides, agar, gelatin, keratin, carboxymethylcellulose, hyaluronic acid, alginic acid, silk, wool, natural rubber and many others.

Other examples of hydrophilic gelling agents include silicone gelling agents: polysiloxanes, other silicone polymers, and silicon oils. These groups contain numerous polymers that can be classified as liquid, elastomers, and resins. Further examples of gelling agents include cellulose ethers and esters, starch and fermentation products, protein-based polymers, exudate and vegetable gums, marine polymers, natural phenolics and polyphenols, and others.

Examples of gum resins are *galbanum*, myrrh, asafetida, creosote, bush resin, okra gum, and ammoniac resin. Examples of thermosetting synthetic resins are phenolics, unsaturated polyesters, polyurethanes, amino resins and epoxy resins. Examples of thermoplastic synthetic resins are polyethylene, polypropylene, polystyrene, acrylonitrile/butadiene/styrene (ABS), polyethylene terephthalate (PET), polyvinyl chloride (PVC), polycarbonate, nylon, thermoplastic elastomers (TPE), liquid crystal polymers, acetals, polyurethane, and thermoplastic polyester.

As used herein, the terms "hydrophilic HASA-gel composition" or "hydrophilic HASA-gel mixture" refer to a mixture of a therapeutically effective amount of a HASA and at least one hydrophilic gelling agent. This hydrophilic HASA-gel composition or mixture is an intermediate composition that occurs prior to applying at least one of a crosslinking agent, a thickening agent, or a polymerization agent to the mixture.

The term "hydrophilic HASA-gel matrix" refers to a hydrophilic composition resulting from the use of at least one of a thickening agent, a crosslinking agent, or a polymerization agent with the mixture of a therapeutically effective amount of a HASA and at least one hydrophilic gelling agent (i.e., HASA-gel mixture). The hydrophilic HASA-gel matrix has a viscosity greater than water. Preferably, the hydrophilic HASA-gel matrix does not flow at room temperature.

As used herein, the phrase "test mixture" refers to HASA comprising a homeopathic compound and uninhibited aqueous composition. The test mixture is made by combining the homeopathic compound in a ratio of 1 gram of 50M *Arnica* pellets to 1 cup of either (i) Lake Michigan (Lake Michigan, USA) or (ii) spring water and then stirring 10 times the Lake Michigan water or spring water at a rate of three 3" revolutions per second.

As used herein, the term "control" or "control test mixture" is defined as a test mixture that is unaltered, has no additives, and has not been subjected to any additional processes.

As used herein, the phrase "evaluation product" refers to a test mixture subject to a manufacturing procedure or process to be evaluated.

As used herein, the phrase, "test procedure" refers to a procedure that is completed according to the following described steps. The test site is the posterior hip directly posterior to the Anterior Superior Illiac Spine (ASIS) and at least 1" below the iliac crest. Other locations on the body are suitable provided they provide sufficient soft tissue to test the *arnica*. A 4×4 square inch pad of the control mixture or evaluation product is applied to test site, either directly or by soaking a 4×4 square inch absorbent substrate in the mixture, for 1 hour and covered by a water barrier. The application is removed and a 3 lb. metal bar of 1.0 inch diameter is dropped 20 inches down a 2 inch diameter tube on to the skin onto the location where the pad was applied. The 4×4 square inch pad is then replaced over the area impacted by the bar and covered by a water barrier, to ensure it will not dry out, for another 12 hours. No pressure may be applied to the application site for the duration of the test. The bruise is photographed for 20 days.

As used herein, the term "comparative test" refers to a test conducted according to the following described procedure. The evaluation product and the control test mixture are made using the same lot of 50M *Arnica* pellets. The test can be used for evaluating any method of manufacturing for any homeopathic active. Forty subjects are evaluated according to the test procedure. Each subject will be randomized to receive the placebo on one side and an active "control" or "evaluation product" on the other side. The bruises from the test will be photographed for two weeks. The photographic results of the 20 subjects are evaluated by a blinded panel of 3 experts using a 0-10 point scale, 0 being no bruise and 10 being the maximum bruise identified. A purple bruise of any size will be rated a 5 or higher. The results for the evaluation product bruises, placebo and control bruises for bruise color, size, and length of time until the bruise disappears. The difference in the maximum rating on each bruise will be recorded and the difference between the placebo and the active (maximum placebo rating minus the maximum active rating). This difference for the 20 controls and 20 evaluation products will be statistically compared. The two populations (the difference of each 20 person group) are determined to be similar or dissimilar using a Z-test, the Student's t-test, the F-test or the chi-square test. It is likely that the test can be modified over time and possibly a smaller sample size may be made as well as different locations and or impact force as long as they provided data that is statistically similar to this test.

It must be noted that as used herein and in the appended claims, the singular forms "a," "an," and "the" include plural references unless the context clearly dictates otherwise. Thus, for example, reference to "an active agent" includes a plurality of active agents and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

1. The Homeopathic Compound

A medium to high formulation of a homeopathic compound including one or more naturally derived ingredients may be selected and used in the compositions and methods of the present invention.

In one embodiment, the homeopathic compound may comprise known or conventional homeopathic compounds, including any one or more ingredients disclosed in the HPUS; Boericke, William, "Pocket Manual of Homeopathic Materia Medica," B. Jain, 1995; Hahnemann, Samuel, "Materia Medica Pura," 1830; or Schroyens, Frederik, "Synthesis Repertory 9," Homeopathic Book Publishers, 2004 herein incorporated by reference. Exemplary homeopathic compounds for use in formulating the compositions of the invention may include homeopathic compounds suitable for treating tissue damage, including deep tissue damage, such as that caused by surgery, superficial wounds, and skin diseases, as well as any condition associated with a severe injury or ailment, pain, inflammation or infection. Tables 1-3 (below) provides a list of exemplary compositions and/or ingredients that are particularly effective for treating localized ailments or injuries, any one of which or combinations thereof, may be used to formulate the homeopathic compound of the present invention. In one embodiment, the homeopathic compound may also include any of the ingredients or combinations thereof listed in Table 4 below.

In exemplary embodiments, the homeopathic compound may include one or more ingredients selected from *Arnica Montana* (*Arnica*), *Bellis perennis*, *Calendula*, *Hypericum perforatum* (*Hypericum*), *Ledum palustre* (*Ledum*), *Ruta graveolens* (*Ruta*), *Symphytum officinale*, *Rhus toxicodendron* (*Rhus Tox*), *Staphasagria*, or *Natrum Sulphuricum*. In other exemplary embodiments, the homeopathic compound may include a combination of only *Arnica montana*, *Ledum palustre*, *Ruta graveolens*, and *Rhus toxicodendron*. Alternatively, the homeopathic compound may include a combination of only *Arnica montana* and *Ledum palustre*. In still other exemplary embodiments, the homeopathic compound may include a combination of only *Arnica montana*, *Ledum palustre*, *Ruta graveolens*, *Rhus toxicodendron* and *Hypericum perforatum*.

TABLE 1

| Injuries | |
|---|---|
| GENERALS INJURIES | RN., CALEN., CAMPH., CANN I., CON., REP., HYPER., PULS., RHUS T., RUTA., SUL AC., SYMPH. A |
| GENERALS INJURIES operation Wound | -STAPH. |
| GENERALS INJURIES overexertion, strain | BELL P., CALC. |
| GENERALS INJURIES concussion | ARN., BAD., HYPER., NAT S. |
| GENERALS INJURIES contusion | RUTA |
| GENERALS INJURIES Bones; fractures of | CARB AC., HYPER., RUTA, SPIG., SYMP. |
| HEAD INFLAMMATION Brain | BELL. |

TABLE 1-continued

| Injuries | |
|---|---|
| HEAD INJURIES of the head; | ARN., NAT S |
| HEAD INFLAMMATION Periosteal | FL AC., MEZ., PH AC. |
| HEAD INFLAMMATION Brain | ACON., ARN., BELL., HYPER., NAT S., SIL. |
| HEAD INFLAMMATION Meninges | BELL, HELL., STRAM., ZINC. |
| HEAD PAIN injuries; after mechanical | NAT S. |
| GENERALS SHOCK injuries | ACON., ARN., CAMPH., DIG., HYPER., LACH., OP., VERAT. |
| GENERALS INJURIES sprains | AGN., ARN., CALC., LYC., MILL., NAT C., NAT M., PETR., PHOS., PLAT., RHUS T., RUTA, STRAM. |
| GENERALS INJURIES Periosteum, of | CALC., RUTA, SPONG., SYMPH. |
| GENERALS INJURIES tennis elbow | AGAR., AMBR., RHUS T. |
| GENERALS INJURIES rupture | ARN., CALC., CALEN., NAT C., NAT M., PHOS., RHUS T. |
| GENERALS INJURIES Nerves | ALL C., ARN., BELL., HELON., HYPER., LED., MENY., PH AC., PHOS. |
| GENERALS INJURIES Soft parts, of | ARN., CON. |
| GENERALS INJURIES Tendons, of | ACON., AM C., ANAC., APIS, ARN., ARS., ARS I., BELL., BENZ AC., BRY., CALC P., CALEN., CANTH., FERR., GUAJ., HEP., IOD., KALI I., RHOD., RHUS T., RUTA, SIL., SULPH., SYMPH., THUJ. |

TABLE 2

| Acute Ailments | |
|---|---|
| SKIN-ERUPTIONS boils | ARN., BELL., HEP., LACH., LYC., MERC., PETR., PSOR., RHUS T., SULPH. |
| SKIN-ERUPTIONS blisters | ANT C., CAUST., RHUS T. |
| SKIN-DECUBITUS | ARN., CHIN., GRAPH., LACH., PETR., SEP., SIL. |
| FACE-ERUPTIONS acne | AUR., CARB AN., CARB V., CARBN S., CAUST., FL AC., GRAPH., REP., KALI AR., KALI BI, KALI BR., LYC., NAT M., NUX V., PHOS., PULS., RHOD., RHUS T., SARS., SEP., SIL., SULPH., SYPH., TEUCR., ZINC. |
| Herpes | AGAR., AM C., ANAN., ARS., BAR C., BOV., CALC., CARB AN., CARB V., DULC., ELAPS, GRAPH., HEP., KALI AR., KALI BI, KALI C., KALI I., KALI S., LACH., LED., LYC., MERC., NAT AR., NAT C., NAT M., NAT S., NICC., NIT AC., PSOR., RHUS T., SEP., SIL., SULPH., THUJ. |
| SKIN ERUPTIONS pustules | ANT T., ARS., RHUS T., STAPH., SULPH. |
| SKIN ERUPTIONS rhus poisoning | ANAC., RHUS D. |
| SKIN ERUPTIONS impetigo | ANT C., ARUM T. |
| SKIN ERUPTIONS granular | ACON., AGAR., ALUM., AM C., ARS., BELL., BRY., BUFO, CARB V., CLEM., COCC., CON., DULC., GRAPH., HEP., IOD., IP., KREOS., LED., MANC., MERC., MERC C., MEZ., NAT M., NUX V., OP., PAR., PH AC., PHOS., PSOR., PULS., RHUS T., SARS., STRAM., SULPH., VALER., VINC., ZINC. |
| SKIN ERUPTIONS herpes zoster | IRIS, MERC., MEZ., RAN B., RHUS T. |

TABLE 3

| Chronic Ailments | |
|---|---|
| SKIN ERUPTIONS lichen | ACON., AGAR., ALUM., AM M., ANAN., ANT C., APIS, ARS., ARS I., BELL., BOV., BRY., CALAD., CASTN V., CIC., COCC., DULC., JUG C., KALI AR., KREO S. , LED., LYC., MANG., MERC., MUR AC., NAT C., NAT M., PHYT., PLAN., RUMX., SEP., SUL I., SULPH., TIL. |
| SKIN ERUPTIONS lichen planus | AGAR., ANAC., ANT C., APIS, ARS., ARS I., CHIN AR., IOD., KALI BI, KALI I., LED., MERC., SARS., STAPH., SUL I., SULPH., SYPH. |
| SKIN ERUPTIONS pemphigus | LACH. |
| SKIN ERUPTIONS petechiae | ARS., BRY., PHOS., RHUS T. |
| SKIN ERUPTIONS pityriasis versicolor | CARB AC., CAUL., DULC., LYC., MEZ., NAT AR., PSOR., SEP., SULPH., TELL. |
| SKIN ERUPTIONS psoriasis | ARS I., LYC., PHYT., SEP. |
| SKIN ERUPTIONS ringworm | ANT C., ANT T., APIS, ARS., BAC., BAPT., BAR M. CALC., CALC I., CHIM., CUPR., DULC., EUP PER., GRAPH., HEP., JUG R., KALI I., KALI S., LAPPA, LYC., MEZ., NAT M., OL J., PHYT., PSOR., RAD BR., RAN B., RHUS T., SEP., SIL., SULPH., TELL., THUJ., TUB., VIOL T. |
| SKIN ERUPTIONS scaly | ARS., CLEM., KREOS., PHOS., PHYT., SEP. |
| SKIN ERUPTIONS scabies | ARS., CARB V., CARBN S., CAUST., KALI S., PSOR. , SEL., SEP., SULPH. |
| SKIN ERUPTIONS scarlatina | AIL., AM C., APIS, BELL., LACH., LYC., MERC., NIT AC., RHUS T. |
| SKIN ERUPTIONS suppurating | ANT C., CHAM., GRAPH., LYC., MERC., NIT AC., PETR., RHUS T., SEP., SIL. |
| SKIN EXCRESCENCES | CALC., CAUST., GRAPH., LYC., NIT AC., STAPH., THUJ. |
| SKIN EXCRESCENCES condylomata | DULC., LACH., MED., MERC C., NAT S., NIT AC., PH AC., THUJ. |
| SKIN FORMICATION | COCA, LYC., PH AC., RHOD., RHUS T., SEC., SULPH., TARENT. |
| HEAD HAIR falling | AUR., BAR C., CARB V., CARBN S., FL AC., GRAPH., KALI C., KALI S., LACH., LYC., NAT M., NIT AC., PHOS., SEP., SIL., SULPH., THUJ. |
| RECTUM FISSURE | CHAM., GRAPH., MUR AC., NIT AC., RAT., SEP., THUJ. |
| RECTUM FISTULA | AUR M., BERB., CALC., CALC P., CARB V., CAUST., KALI C., NIT AC., SIL |
| RECTUM HEMORRHOIDS | AESC., AGAR., ALOE, ARS., CARB AN., CARB V., CAUST., COLL., GRAPH., HAM., KALI AR., KALI C., KALI S., LACH., LYC., |

TABLE 3-continued

| Chronic Ailments | |
|---|---|
| NOSE EPISTAXIS | MERC I R., MUR AC., NIT AC., NUX V., PAEON., PHOS., PULS., SEP., SULPH. ACON., AM C., AMBR., ANT C., ARN., BELL., BOTH., BOV., CACT., CALC., CALC P., CALC S., CARB V., CARBN S., CAUST., CHIN., CROC., CROT H., FERR PIC., HAM., HYOS., IP., KALI I., LACH., MED. MELL, MERC., MILL., NIT AC., PHOS., PULS., RHUS T., SABIN., SEC., SULPH., TUB. |
| HEAD DANDRUFF | CANTH., CARBN S. GRAPH., NAT M., PHOS., SULPH. |

TABLE 4

| Abbreviations | |
|---|---|
| Acon. (Aco.)--. | Aconitum Napellus |
| Aesc- | -Aesculus Hippocastanum |
| Agar.- | -Agaricus Muscarius. |
| Agn. (Ag c.)-- | Agnus Castus. |
| Ail.-- | Ailanthus Glandulosa. |
| All c. (Cep.)-- | Allium Cepa. |
| Aloe (Alo.)-- | Aloe Socotrina. |
| Alum.- | -Alumina. |
| Ambr. (Amb.)--. | Ambra Grisea |
| Am c.--. | Ammonium Carbonicum |
| Am m.-- | Ammonium Muriaticum. |
| Anac.--. | Anacardium Orientale |
| Ant c.-- | Antimonium Crudum. |
| Ant t.-- | Antimonium Tartaricum. |
| Apis (Ap.)-- | Apis Mellifica. |
| Arn.- | -Arnica Montana. |
| Ars.-- | Arsenicum Album. |
| Ars i.-- | Arsenicum Iodatum. |
| Arum t.-- | Arum Triphyllum. |
| Aur.--. | Aurum Metallicum |
| Bad.-- | Badiaga. |
| Bapt.- | -Baptisia Tinctoria. |
| Bar c.-- | Baryta Carbonica. |
| Bar m.-- | Baryta Muriatica. |
| Bell.--. | Belladonna |
| Bell p.-- | Bellis Perennis. |
| Benz ac.-- | Benzoicum Acidum. |
| Berb.-- | Berberis Vulgaris |
| Both.-- | Bothrops Lanceolatus |
| Bov.--. | Bovista |
| Bry.-- | Bryonia Alba. |
| Bufo (Buf.)-- | Bufo Rana. |
| Cact.-- | Cactus Grandiflorus. |
| Calad.-- | Caladium Seguinum. |
| Calc. (Calc c.)-- | Calcarea Carbonica. |
| Calc-i. (Calc io.)-- | Calcarea Iodata. |
| Calc p.-- | Calcarea Phosphorica. |
| Calc s.-- | Calcarea Sulfurica. |
| Calen. (Calend.)-- | Calendula. |
| Camph. (Cam.) | Camphora. |
| Cann i. (Cann.)-- | Cannabis Indica. |
| Canth-- | Cantharis |
| Carb ac.-- | Carbolicum Acidum. |
| Carb an. (Carb-a.)-- | Carbo Animalis. |
| Carb v.-- | Carbo Vegetabilis. |
| Carbn s.-- | Carboneum Sulphuratum. |
| Caul.-- | Caulophyllum |
| Caust. (Caus.)-- | Causticum. |
| Cham.--. | Chamomilla |
| Chel.-- | Chelidonium Majus. |
| Chim.--. | Chimaphila Umbellata |
| Chin.-- | China Officinalis. |

TABLE 4-continued

| Abbreviations | |
|---|---|
| Chin ar.--. | Chininum Arsenicosum |
| Chlol. (Chi-hyd.)-- | Chloralum Hydratum. |
| Cic.-- | Cicuta Virosa. |
| Clem.-- | Clematis Erecta. |
| Coca-- | Coca. |
| Cocc. (Cocl.) (Coccl.)-- | Cocculus Indicus. |
| Coll.-- | Collinsonia Canadensis. |
| Con.-- | Conium Maculatum. |
| Cop.--. | Copaiva Officinalis |
| Croc.-- | Crocus Sativus. |
| Crot h.-- | Crotalus Horridus |
| Croto t.-- | Croton Tiglium. |
| Cupr. (Cup.)-- | Cuprum |
| Dig.--. | Digitalis Purpurea |
| Dulc.-- | Dulcamara. |
| Elaps.--. | Elaps Corallinus |
| Eup per.-- | Eupatorium Perfoliatum |
| Ferr. (Fer.)-- | Ferrum Metallicum. |
| Ferr pie.-- | Ferrum Picricum |
| Fl ac. (Flu ac.)-- | Fluoricum |
| Graph. (Grap.)-- | Graphites. |
| Guaj.-- | Guaiacum |
| Ham.-- | Hamamelis Virginica. |
| Hell.-- | Helleborus Niger. |
| Helon.-- | Helonias Dioica. |
| Hep.-- | Hepar Sulphuris Calcareum. |
| Hyos. (Hyo.)--. | Hyoscyamus Niger |
| Hyper. (Hypr.)-- | Hypericum |
| Iod.--. | Iodum |
| Ip.-- | Ipecacuanha. |
| Iris (Iris v.)-- | Iris Versicolor. |
| Jug r. (Jugl.)-- | Juglans regia. |
| Kali ar.-- | Kali Arsenicosum. |
| Kali bi.-- | Kali Bichromicum. |
| Kali br. (Kali bro.) (Kali b.)-- | Kali Bromatum. |
| Kali c.-- | Kali Carbonicum. |
| Kali i. (Kali io.)-- | Kali Iodatum. |
| Kali s.-- | Kali Sulphuricum. |
| Kreos. (Kre.)-- | Kreosotum. |
| Lach.-- | Lachesis Trigonocephalus. |
| Lappa (Lappa)-- | Lappa |
| Led.-- | Ledum Palustre. |
| Lyc.-- | Lycopodium Clavatum. |
| Manc.-- | Mancinella. |
| Mang.-- | Manganum. |
| Meli.-- | Mellilotus Officinalis. |
| Meny. (Men.)-- | Menyanthes |
| Merc. (Merc.) (Merc viv.)-- | Mercurius. |
| Merc c. (Mer cor.)-- | Mercurius Corrosivus. |
| Merc I r.-- | Mercurius Iodatus Ruber. |
| Mez.-- | Mezereum. |
| Mill.-- | Millefolium. |
| Mur ac.-- | Muriaticum Acidum. |
| Nat ar.-- | Natrum Arsenicicum. |
| Nat c.-- | Natrum Carbonicum. |
| Nat m.-- | Natrum Muriaticum. |
| Nat s.-- | Natrum Sulphuricum. |
| Nicc.-- | Niccolum. |
| Nit ac.-- | Nitricum Acidum. |
| Nux v.-- | Nux Vomica |
| Ol j.-- | Oleum Jecoris Aselli |
| Op.-- | Opium. Paeon. |
| (Pae.)-- | Paeonia Officinalis. |
| Par.-- | Paris Quadrifolia |
| Petr.-- | Petroleum. |
| Ph ac. (Pho ac.)-- | Phosphoricum Acidum. |
| Phos. (Pho.)-- | Phosphorus. |

TABLE 4-continued

Abbreviations

| | |
|---|---|
| Phyt.-- | Phytolacca Decandra. |
| Plan. (Plant.)-- | Plantago Major. |
| Plat.-- | Platinum |
| Psor. --. | Psorinum |
| Puls. (Pul.)-- | Pulsatilla Nigricans. |
| Rad br. (Radm.)-- | Radium Bromatum. |
| Ran b.-- | ranunculus Bulbosus. |
| Rhod. (Rho.)-- | Rhododendron Chrysanthum. |
| Rhus d-- | Rhus Diversiloba |
| Rhus t.-- | Rhus Toxicodendron. |
| Rumx. (Rum.)--. | Rumex Crispus |
| Ruta (Rut.)-- | Ruta Graveolens. |
| Sabin. (Sabi.)-- | Sabina. |
| Sars.-- | Sarsaparilla. |
| Sec. (Sec c.)-- | Secale Cornutum. |
| Sep.-- | Sepia Officinalis. |
| Sil.-- | Silicea |
| Spig. (Spi.)-- | Spigelia Anthelmia. |
| Spong.-- | Spongia Tosta |
| Staph. (Stap.)-- | Staphisagria. |
| Stram. (Stra.)-- | Stramonium. |
| Sul i. (Sul io.)-- | Sulfur Iodatum. |
| Sulph. (Sul.)--. | Sulphur |
| Sul ac.-- | Sulphuricum acidum. |

The homeopathic compound of one or more ingredients thereof may be used to treat an ailment or injury for which it is known to be effective in accordance with any conventional homeopathic practice, such as that set forth in any homeopathic material Medica, HPUS or other homeopathic treatment guide. Alternatively, the homeopathic compound may be used to treat an ailment or disease for which it has not been previously recognized as effective. As is the convention with homeopathic medicine, a single homeopathic compound may also be used to treat multiple different ailments or injuries. For example, a single homeopathic compound may be used to treat migraines, trauma to the eye, or sinusitis, as detailed in the homeopathic Materia Medica.

It will be recognized by those skilled in the art that the compositions and treatments described herein are effective in treating humans as well as animals known to suffer the types of injuries that can be treated by the present invention. Suitable examples of the types of vertebrates that may be treated include, but are not limited to, cows, dogs, goats, horses, cats, chickens, humans, rabbits, hares, wolves, mice, rats, sheep, pigs, foxes, and non-human primates, as well as any reptile or bird species.

The homeopathic compound need not include counterirritant ingredients, and thus, does not rely upon the principal of producing a less severe pain to counteract a more intense pain. Consequently, the homeopathic compound may, but is not required to incorporate menthol, methyl salicylate, or trolamine salicylate. Additionally, the homeopathic compound may, but need not, include a chemical penetration enhancer such as alcohols, sodium lauryl sulphate, Pluronic F68, or similar substances.

The homeopathic compound is formulated to have a medium to high potency and may be prepared in accordance with any method, such as that described in disclosed in the HPUS; Boericke, William, "Pocket Manual of Homeopathic Materia Medica," B. Jain, 1995; Hahnemann, Samuel, "Materia Medica Pura," 1830; or Schroyens, Frederik, "Synthesis Repertory 9," Homeopathic Book Publishers, 2004. In one embodiment, the homeopathic compound of the present invention has a medium to high potency of at least about 30 C. Alternatively, the homeopathic compound may have one potency of at least about 200 C, at least about 400 C, at least about 1M, at least about 2M, at least about 5M, at least about 10M, at least about 20M, at least about 50M, at least about 1 CM, at least about 2 CM, at least about DM, at least about MM, any intermediate potency in between, or any higher potency thereof, such as quintamillesimal (LM or Q) order potencies. Alternatively the compound can be diluted to a dilution factor of $10^{-4}$, $10^{-6}$, $10^{-8}$, $10^{-10}$, $10^{-12}$, $10^{-20}$, $10^{-60}$, $10^{-100}$, $10^{-200}$, $10^{-400}$, $10^{-600}$, $10^{-1000}$, $10^{-10000}$, $10^{-100000}$, $10^{-1000000}$, $10^{-10000000}$, $10^{-100,000,000}$, $10^{-1,000,000,000}$ for example. It is understood that the dilutions are examples only and that any dilution factor within that range of from $10^{-4}$ to $10^{-1,000,000,000}$ and even greater are also contemplated by this disclosure. Mixing of different potencies of the same or different homeopathic compounds and/or ingredients is also contemplated to be within the scope of the present invention. For example, a 1M *arnica* can be mixed with a 10M *arnica* or 10M *Ledum*. Therefore, the homeopathic compound of the invention can be varied in terms of ingredients, potency or dosages as described herein.

In one embodiment, exposure to direct sunlight, higher temperatures, volatile organic compounds, x-rays, and electromagnetic fields should be avoided during formulation, storing and shipping in order to prevent a change or neutralization in potencies. Preferably, the homeopathic formulation may be packaged in plastic, glass or other containers following HPUS, GMP's and all OTC regulations.

2. Homeopathic Aqueous Substance Active or HASA

The HASA generally includes a combination of a homeopathic compound having potency of at least 6 C or a dilution factor of at least $10^{-4}$ and an uninhibited aqueous composition. As noted in section 1, the homeopathic compound may include any of a variety of known homeopathic substances, including, but not limited to, *Arnica montana, Bellis perennis, Calcarea phosphorica, Calendula, Hypericum perforatum, Ledum palustre, Rhus toxicodendron, Millefolium, Ruta graveolens, Symphytum officinale, Apis Mel, Cantharis, Urticartia Urens, Belladonna, Ferrum Metallicum, Staphasagria, Hepar Sulphuricum, Euphatorium perfoliatum, Bryonia, Naturm Sulphuricum, Calcarea carbonica* and *Hamamelis*, and combinations thereof. As stated previously, the homeopathic compound may be present in a broad range of potencies, ranging from at least 6x, 12 C or 30 C to at least 1000M, or alternatively a dilution factor of from $10^{-4}$ to $10^{-1000000000}$. It should be further understood that the uninhibited aqueous composition may be combined with other substances such as alcohol, juice, salt, etc. that do not affect the formation of HASA. Each added substance must be tested according to the comparative test in order to verify that it has not detrimentally affect the ability to form HASA.

It has been discovered that when a homeopathic compound is combined with an uninhibited aqueous composition it creates a different entity, similar to the way that sodium and chloride form salt. This entity, which is called a HASA, has properties that are unique due to the chemical, energy, structural and other interactions between the uninhibited aqueous composition and the homeopathic compound. It is believed that not all forms of water can be used to form HASA. The water molecules must be similar to that found in natural water such that they may form formations or structures that result in an HASA. Also water that is affected by hydrophilic gelling agents may not form HASA. One method that can be used to determine whether water is an uninhibited aqueous composition is to perform the comparative test. Any other methods that detect effectiveness of the final composition can also be used.

Some examples of the types of water that may be used to form HASA include pure water, fresh water, hard water, soft water, brackish water, seawater, distilled/demineralized water, reverse osmosis water, boiled water, raw water, rain water, snow water, filtered water, steam condensate, boiler feed water, cooling water, waste water, process or hydrotest water/firewater, artesian water/artesian well water, fluoridated water, mineral water, purified water, sparkling water, spring water, sterile/sterilized water, well water, utility water, drinking water, softened water, municipal/tap water, soda water, seltzer water, tonic water, non-potable water, potable (drinkable) water, USP purified water, USP water for injection, USP sterile water for injection, USP sterile water for inhalation, USP bacteriostatic water for injection, USP sterile water for irrigation, deionized water, and combinations thereof.

In one embodiment, the HASA may be produced by combining 2 No. 10 pellets in 4 ounces of water or in half gallon of water and stirring vigorously. In another embodiment, the homeopathic compound is provided in water directly from the manufacturer and added to the hydrophilic gelling agent. In another embodiment, HASA is produced by taking 2 drops of a homeopathic compound provided by the manufacturer and putting it 4 oz of water or ½ gallon of uninhibited water and shaking or agitating the mixture.

In another embodiment, the HASA combined with the hydrophilic gelling agent, prior to or during the process of crosslinking or thickening these hydrophilic gelling agents. For example, a hydrophilic HASA-gel matrix may be formulated by premixing at a ratio of 2 No. 10 pellets of a homeopathic compound in 4 ounces of uninhibited water and stirring vigorously, afterward to which hydrophilic gelling agents are added.

It is believed that the ability to form HASA when exposed to a hydrophilic gelling agent will depend on the ratio of water to hydrophilic gelling agent, such as a hydrophilic polymer, the distance between hydrophilic gelling agents, the hydrophilic strength, the amount of light and a number of other factors. Because it may be difficult to control for all of these factors, it may be desirable to verify that a particular combination has not affected the efficacy of the homeopathic product. Thus, it may be desirable to determine if HASA forms for a particular product by conducting the comparative test or any other test that verifies the formation of HASA for any water type, hydrophilic polymer or gelling agent, or HASA-gel matrix. Based on the success forming HASA for *arnica* demonstrated below, the other homeopathic compounds are likewise expected to form HASA at various potencies.

3. Hydrophilic HASA-Gel Composition (Intermediate Composition)

As previously noted, it is preferred that the HASA be formed first before it is added to the gelling agent. Likewise, it is preferred that the HASA and the gelling agent are combined before the hydrophilic HASA-gel matrix is formed by use of at least one of a thickening agent, a crosslinking agent, or a polymerization agent. Accordingly, one aspect of the invention is an intermediate compositions comprising a therapeutically effective amount of a HASA and at least one hydrophilic gelling agent, wherein the HASA comprises a homeopathic compound having potency of at least 6 C or a dilution factor of at least $10^{-4}$ and an uninhibited aqueous composition. In other words, this aspect is the mixture of the HASA and the gelling agent before the gel is formed.

4. Hydrophilic HASA-Gel Matrix

Once the mixture of the HASA and the gelling agent is prepared, it may then be formed into a hydrophilic HASA-gel matrix by applying at least one of a thickening agent, a crosslinking agent, or a polymerization agent.

In one embodiment, the HASA-gel matrix may be a composition of a minimum of 41% HASA and a gel base.

During the preparation of the HASA-gel matrix, it is desirable that the HASA-gel mixtures not be exposed to conditions that decrease the effectiveness of the HASA. For example, high temperature carriers are not preferred as they are gelled at temperature in excess of approximately 121° F. to approximately 158° F., depending on the carrier, which is known to result in a reduction of the effectiveness according to the HPUS. Most hydrogels require UV, electron beam or temperatures in excess of 121° F. to 158° F. to crosslink or gel. Because high temperatures can decrease the effectiveness of the HASA, preferably, temperatures below 158° F., more preferably temperatures below 145° F., more preferably temperatures below 140° F., more preferably temperatures below 135° F., more preferably temperatures below 130° F., more preferably temperatures below 125° F., and most preferably temperatures below 121° F. are used to form a hydrophilic HASA-gel matrix according to the methods of this invention. Importantly, any high energy process has the potential to destroy HASA, not just temperature. Thus, HASA may become compromised if exposed to high energy processes, such as UV or electron beams, even though it is never exposed to a high temperature. Some substances may be effective even when exposed to 121° F. or higher. The method of verifying that the HASA has not been affected is verifying that the evaluation product performs similarly to the control test mixture, as defined previously, for the comparative test, demonstrating a significant improvement in the treatment of tissue damage, when compared to placebo. In one embodiment, the verification that HASA has not been affected may be established if both the evaluation product and the control test mixture result in a statistically significant improvement in bruising scores after performing a comparative test, when compared to placebo. Statistical significance may be established as a p-value less than 0.2, less than 0.15, less than 0.1, less than 0.05, and less than 0.01. However, it should be understood that any method for verifying the formation and preservation of HASA is acceptable in accord with the current invention.

In one embodiment, the homeopathic compound contains a sufficient amount of water to prevent the HASA from becoming substantially absorbed or substantially metabolized by the body before completion of the prescribed or predetermined treatment period. One skilled in the art will appreciate that the amount of water will depend on the desired length of treatment or prophylaxis. A therapeutically effective amount of HASA to be used can be determined by using at least the comparative test. For example, a therapeutically effective amount of HASA can be at least 41% HASA. The percentages of HASA are by weight of the composition, unless stated otherwise. In another embodiment, a therapeutically effective amount of HASA can be at least 45% HASA, at least 50% HASA, at least 55% HASA, at least 60% HASA, at least 65% HASA, at least 70% HASA, at least 75% HASA, at least 80% HASA, at least 85% HASA, at least 90% HASA, at least 95% HASA, or at least 100% HASA. More preferably, the therapeutically effective amount of HASA may be between 41% and 100% HASA; more preferably, the therapeutically effective amount of HASA may be between 41% and 80% HASA; more preferably, the therapeutically effective amount of HASA may be between 41% and 60% HASA; and more preferably, the therapeutically effective amount of HASA may be between 41% and 50%. In further embodiments, the therapeutically effective amount of HASA may be between 50% and 60%.

The hydrophilic HASA-gel matrix of this invention, preferably, contains 1-59% gel; more preferably, 1-55% gel; more preferably, 1-50% gel; more preferably, 1-45% gel; more preferably 1-40% gel; more preferably 1-35% gel; more preferably, 1-30% gel; more preferably 1-25% gel; and more preferably 1-20% gel, where the percentages are weight to weight of the composition, unless stated otherwise.

The preferred types of hydrophilic gels were described above.

Preferably, the thickening agent, crosslinking or polymerization agents include at least one of cellulose, a cellulose derivative, acacia, agar, alginate, carrageenan, gum tragacanth, xanthan gum, collagen, carboxypolymethylene, glyceryl monostearate, polyvinylpyrrolidone, and polyacrylamide, temperature, pressure, change in pH, radiation (e.g., ultraviolet light, gamma radiation, or electron beam radiation), or a chemical crosslinking agent.

In certain embodiments, the compositions of the present invention may include optional excipients, additives, preservatives, antioxidants, stabilizers, surfactants, pH-modifying agents, or any other desirable agents.

The optional one or more inert excipients generally include any excipients known within the art of homeopathic medicine, and may include penetration enhancers, preservatives, antioxidants, surfactants, pigments, dyes, pH modifying agents, thickeners, binders, and combinations thereof, so long as the inert excipient does not compromise HASA. Specifically, the skilled artisan will appreciate that any formulation excipient or additive known within the art of topical homeopathic formulations may be incorporated into the homeopathic compounds of the present invention. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The preservatives may include, but are not limited to preservatives such as benzyl alcohol, trichlorobutanol, p-hydroxybenzoic esters, n-butanol, and methylparaben.

The homeopathic compositions of the present invention can be combined with antioxidants or stabilizers to prevent degradation due to oxidation or other means. Antioxidants include but are not limited to butylated hydroxytoluene (BHT), ferrous sulfate, ethylenediamine-tetraacetic acid (EDTA), or others. Stabilizers include, but are not limited to, amglene, hydroquinone, quinine, sodium metabisulfite or others.

The homeopathic compositions of the present invention may also include one or more surfactants. The surfactant may include anionic surfactants, nonionic surfactants, amphoteric and zwitterionic surfactants, and cationic surfactants. Non-limiting examples of anionic, nonionic, amphoteric, zwitterionic, and cationic surfactants suitable for use in the compositions of the present invention are described in McCutcheon's, Emulsifiers and Detergents, (1989), published by M. C. Pub. Co., and in U.S. Pat. Nos. 2,438,091; 2,528,378; 2,658,072; 3,155,591; 3,929,678; 3,959,461; 4,387,090; 5,104,646; 5,106,609; and 5,837,661, all of which descriptions are incorporated herein by reference.

The compositions described herein may further include pH-modifying agents. The pH-modifying agents suitable for use include, but are not limited to, potassium hydrogen phthalate, and solid organic acids such as citric acid, glutamic acid, maleic acid, d,l-malic acid, glutaric acid, isophthalic acid, succinic acid, fumaric acid, adipic acid, and the like, and mixtures thereof.

The hydrophilic HASA-gel matrix of the present invention may also incorporate a binder to supplement gelling agents and the cohesive qualities of the formulations. Suitable examples of binders include, but are not limited to methylcellulose, sodium carboxymethycellulose, hydroxypropylmethylcellulose, carbomer, polyvinylpyrrolidone, acacia, guar gum, xanthan gum and tragacanth.

Preferably, the aqueous medium is a substance that does not irritate the skin, mucosal lining or other topical application surfaces. In one embodiment, the HASA may be formulated by mixing a homeopathic compound or a sucrose or lactose tablet homeopathic compound in water and/or a water-containing azeotropic mixture.

In certain embodiments, the hydrophilic HASA-gel matrix may be in a form of a sheet having two major surfaces, the a first surface (i.e., the surface that is, typically, the furthest from the place of contact of the sheet with the bodily surface) and a second surface (i.e., the surface that is, typically, in direct contact with the bodily surface and opposite the external surface). In certain embodiments, external layers may be affixed to the first, second or both surfaces of the HASA-gel sheet. For example, at least one external layer may be affixed to the first surface of the gel sheet. The at least one external layer may include at least one of impermeable, semi-permeable or permeable layers. For purposes of preventing the gel from drying out and preventing foreign matter out of the gel, the external layer (the side not in contact with the body) is impermeable. In certain embodiments, a permeable layer may be affixed to the first surface of the gel sheet opposite the side contacting the body surface. The hydrophilic HASA-gel matrix may, alternatively, be in a flowable form.

To date, it has not been appreciated that HASA needs to be formed prior to the introduction of the hydrophilic polymers or, specifically, at least one hydrophilic gelling agent. Surprisingly, it is advantageous to first form HASA and then combine the HASA with at least one hydrophilic gelling agent prior to the formation of the finished gel, i.e., the hydrophilic HASA-gel matrix.

5. Method of Making the Hydrophilic HASA-Gel Matrix

In another aspect, the current invention relates to a method for producing the hydrophilic HASA-gel matrix. The method includes combining a homeopathic compound and an uninhibited aqueous composition to produce HASA. The HASA is then combined with at least one hydrophilic gelling agent. Thereafter, the hydrophilic HASA-gel matrix is formed by use of at least one of a thickening agent, a crosslinking agent, or a polymerization agent. As noted previously, it is important that the process not include any steps or processes resulting in exposure of HASA (before the uninhibited aqueous composition is combined with the homeopathic compound) to a hydrophilic substance that would prevent HASA from forming. As noted previously, the exposure to the hydrophilic substance may include any process or step that impedes the ability of water molecules to freely move, bond and/or clump, or that restricts the natural movement of individual or groups of water molecules.

Additionally, even after HASA has been combined with at least one hydrophilic gelling agent to produce a homeopathic dosage form, high-energy processes that could adversely affect HASA must be avoided at all times leading up to and during the time in which the composition is utilized to treat tissue damage. In one embodiment, the high-energy processes may include ultraviolet light exposure, electron beam exposure, or high temperatures in excess of 121°–158° F.

It should be understood that the hydrophilic HASA-gel matrix of the current invention may comprise any dosage form suitable for delivery of the homeopathic compound to a site where tissue damage is established or is anticipated. Non-limiting examples of dosage forms that may incorporate HASA include gels, including hydrogels, creams, ointments, salves, balms, lotions, liniments, cream gels, lotion ointments and decoctions and combinations thereof.

In accordance with one aspect of the invention, HASA and the hydrophilic gelling agents are combined prior to crosslinking, polymerization or thickening. This yields a highly efficient and cost effective manufacturing process. The resultant hydrophilic HASA-gel matrix may be distributed in a tube of gel, sheet or cream. Furthermore, the hydrophilic HASA-gel matrix may be manufactured and distributed in a hydrated or dried form. In addition, the hydrophilic HASA-gel matrix may be placed on another hydrogel such as an e-beam hydrogel that provides the tackiness to hold it in place. This allows the product to be applied directly to the subject.

In another embodiment, the HASA may be combined with the hydrophilic gelling agent, prior to or during the process of crosslinking or thickening these hydrophilic gelling agents. For example, a hydrophilic HASA-gel matrix may be formulated by premixing at a ratio of two No. 10 pellets or two drops of a homeopathic compound in 4 ounces of uninhibited water and stirring vigorously, to which hydrophilic gelling agents are added.

When the HASA is present during crosslinking, plasticizing, or thickening, the hydrogels may be synthesized by the process of e-beam radiation, gamma radiation, U.V. radiation, chemical, or temperature cross-linking as long as they do not affect the efficacy. One manner of determining if the efficacy has been changed is the comparative test.

In another embodiment, the HASA combined with the hydrophilic gelling agent, after the process of crosslinking these hydrophilic gelling agents. For example, after synthesis, the hydrogel carrier may be immersed in an HASA to become potentized. The hydrogel substrate should be exposed to the HASA for a sufficient amount of time, to ensure adequate HASA is absorbed in order to be therapeutic. In this case the hydrogel acts like a sponge. A minimum of 41% HASA by weight is recommended.

A hydrated hydrogel carrier and HASA may also be separately packaged and distributed. The end user would be instructed to combine HASA and hydrated hydrogel carrier to form the hydrophilic HASA-gel matrix by soaking the sponge sufficiently for it to absorb sufficient HASA to be therapeutic. Upon imbibing the hydrated hydrogel carrier with HASA, the hydrated HASA-gel matrix would then be ready for use. For example, this post-loading method may involve instructing a user to soak a hydrated hydrogel substrate in the HASA mixture for about 3 hours or more before topically administering the hydrated HASA-gel matrix to a site of injury or ailment. In another embodiment a hydrated hydrogel may be immersed in HASA for about 1 hour before topical administration.

The hydrophilic HASA-gel matrix may also be packaged and distributed as a dry product, wherein the hydrogel carrier and HASA are either separately packaged and distributed as dried compounds or may be packaged and distributed as a dried mixture. In this embodiment, the HASA and hydrogel may be directly formulated as a dry product, such as a powder or other solid, or may be subsequently dehydrated to achieve a dried form. The end user may then be instructed to immerse the produce HASA by combining 2 No. 20 pellets in 4 ounces of tap water and stirring it 10 times. The hydrogel carrier may then be imbibed with HASA by immersing the hydrogel carrier in HASA for a predetermined period of time, allowing the hydrogel carrier to absorb the HASA in sufficient quantities to be therapeutic.

Optionally, after the HASA-gel matrix is hydrated, subsequent administrations of water or other fluids containing water may be intermittently added to the hydrated HASA-gel matrix in order to extend the duration in which the HASA is maintained in an aqueous environment. In one embodiment, the subsequent administrations of water or fluids containing water may be directly delivered to the HASA-gel matrix at the site of injury. Alternatively, the water or fluid containing water may be added to a dressing, such as a gauze pad or bandage, on which the HASA-gel matrix is delivered.

In another embodiment, the patient's bodily fluids and secretions alone may provide the requisite amount of water to extend the duration that the HASA is maintained in an aqueous environment during topical administration. For example, bodily fluids and secretions produced by open wounds, mucous membranes, pores, and/or tears ducts may contain a sufficient quantity of water to extend the duration that the hydrophilic HASA-gel matrix is maintained in an aqueous environment during treatment so as to minimize or avoid the need for subsequent administrations of water or water containing fluids or for the re-application of the hydrophilic HASA-gel matrix.

At the time of topical application, the hydrogel carrier is hydrated so as to contain a sufficient amount of water capable of maintaining the HASA in an aqueous environment and in contact with the skin so as to prevent the HASA from becoming completely absorbed or completely metabolized by the body before completion of the prescribed or predetermined treatment period. In another embodiment, when hydrated, the hydrogel carrier contains about 40% by weight or more of water. Alternatively, the hydrogel contains up to and including about 98% by weight water. This water may be obtained from any water containing liquid medium, including bodily fluids. In one embodiment, when a dried hydrogel carrier and an aqueous or dry HASA-gel matrix are exposed to a bodily fluid, the bodily fluid may contain a sufficient amount of water molecules for delivering and maintaining the hydrophilic HASA-gel matrix in an aqueous environment.

The hydrogel carrier is further capable of maintaining the HASA in an aqueous environment and in contact with the site of an ailment or injury for at least the prescribed treatment period. Without wishing to be bound by theory, it is believed that the aqueous environment both initiates and provides for the continued therapeutic activity of the HASA throughout the duration in which the HASA is maintained in the aqueous environment. Moreover, without wishing to be bound by theory, it is further believed that maintaining a HASA in an aqueous environment provides superior therapeutic results.

The aqueous environment is achieved by the preferred unique three dimensional hydrophilic polymeric network of the hydrogel, which provides a reservoir of water, similar to a sponge. This continuous supply of water enables the formulation of the HASA at high potency levels at the site of the injury when applied, injected or inserted to the body. By comparison, conventional gels do not have this three dimensional hydrophilic polymeric network and are readily absorbed and metabolized by the body. 6. Administering Hydrophilic HASA-Gel Matrix After the medium or high potency hydrophilic HASA-gel matrix is formulated, the hydrophilic HASA-gel matrix may be topically administered to a patient.

Specifically, the hydrophilic HASA-gel matrix may be topically applied directly onto one or more bodily surfaces, including any tissue, such as epithelial tissue, connective tissues, nervous tissues; any subcutaneous surface; muscles; organs; nerves; brain; arteriol; lymphatic; bone or combinations thereof. In another embodiment, the composition may be topically administered to the skin, eyes, ears, or mucosal lining of the nasal or anal cavity of a vertebrate, such as, but not limited to, a human.

Topical administration involves applying the hydrophilic HASA-gel matrix directly to the bodily surface and maintaining contact with the surface so that at least some of the HASA remains active and does not substantially become absorbed or otherwise metabolized until the end of the treatment period. The term "treatment period" refers to the time that the hydrophilic HASA-gel matrix is in direct contact with the bodily surface and maintains contact with the surface so that at least some HASA remains active. For example, the treatment period may include pre-application of the hydrophilic HASA-gel matrix prior to the injury, application of hydrophilic HASA-gel matrix post injury, or both.

The hydrophilic HASA-gel matrix immediately becomes effective upon application to the bodily surface but becomes more therapeutic the longer it is applied, similar to a pain patch medication. While not wishing to be bound by theory, it is believed that the direct contact between the bodily surface and hydrophilic HASA-gel matrix while maintained in an uninhibited aqueous environment extends the activity of and consequently increases the therapeutic effectiveness of the hydrophilic HASA-gel matrix.

The homeopathic compound of the present invention should be designed to maintain the homeopathic compound in an aqueous environment, by, for example, keeping the site of an ailment or injury wet with the HASA for an extended period of time, at least for the prescribed treatment period.

In one embodiment, the patient's bodily fluids may provide the required aqueous environment and/or assist in maintaining the HASA in an aqueous environment during administration. For example, bodily fluids produced by open wounds or mucous and/or tears produced by the eye may produce a sufficient quantity of aqueous medium molecules to maintain the homeopathic compound in an aqueous environment during treatment. Bodily fluids alone may include a sufficient quantity of water molecules to maintain the homeopathic compound in an aqueous environment sufficient for effective administration. For example, in instances wherein the homeopathic compound is administered to a mucosal membrane, the natural water-containing secretions of the mucosal membrane may maintain the homeopathic compound in an aqueous environment, such that the amount of uninhibited aqueous composition may be relatively small.

The hydrophilic HASA-gel matrix may be intermittently or continuously re-applied as necessary so as to provide either a continuous dosage or multiple dosages over time.

In another embodiment, the hydrophilic HASA-gel matrix may be administered directly to the site of an ailment or injury. Conventional knowledge in the art of homeopathic medicine suggests that high potency topical compositions would be sublingually administered so as to provide a primarily systemic treatment and only limited, if any, to localized therapy. However, when administered to the site of an ailment or injury and maintained in an aqueous environment, the hydrophilic HASA-gel matrix of the current invention is capable of delivering a direct localized treatment at high potency to a dry surface.

In another embodiment, the hydrophilic HASA-gel matrix may be topically administered so as to completely cover the area of ailment or injury. Alternatively, smaller or larger topical administration areas are also contemplated.

Alternatively, the delivery mechanism may be a continuous release of HASA from the hydrophilic HASA-gel matrix, designed to release the HASA for an extended period of time and/or interact with a bodily surface, such as a mucosal membrane or bodily fluid, to continuously release the HASA. The continuous release must be able to maintain the HASA in an aqueous environment and in contact with a bodily surface for the duration of the treatment. In another embodiment, for HASA intended to be topically administered to the skin, the hydrophilic HASA-gel matrix may include a means for maintaining the homeopathic product dissolved in an aqueous medium that contains a sufficient amount of water molecules so that not all of the HASA-gel matrix does not become absorbed, metabolized or evaporated in a time frame less than the requisite treatment period.

Optionally, topical application of the hydrophilic HASA-gel matrix need not, but may be combined with iontophoresis, a transdermal patch, electroporation, sonophoresis, phonophoresis, massage, or application of pressure to the site of administration. Furthermore the method of the present invention (to be described herein) may be optionally performed in conjunction with any conventional homeopathic treatment, including any oral or other topical administrations.

In one embodiment, exposure to direct sunlight, high temperatures, volatile organic compounds, X-rays, and electromagnetic fields is preferably avoided during topical administration of the hydrophilic HASA-gel matrix. 7. Hydrophilic HASA-Gel Matrix for Treatment of an Ailment or Injury The compositions and methods of the present invention may be used to effectively treat any ailment or injury, particularly acute and chronic ailments or injuries.

The hydrophilic HASA-gel matrix of the present invention is most effective when it is administered before or relatively immediately after incurring the ailment or injury.

To effectively treat inflammation, the hydrophilic HASA-gel matrix may be repeatedly administered until the acute inflammation phase is complete, wherein there is no increase in swelling upon removal of the HASA-gel matrix.

For acute ailments or injuries, such as inflammation, pain, ecchymosis, boils, epistaxis, skin diseases, such as blisters, impetigo, tinea, herpes zoster, surgical injuries and herpes, the topically applied high potency hydrophilic HASA-gel matrix may be continuously administered until the ailment or injury is effectively treated. To effectively treat pain, the hydrophilic HASA-gel matrix may be repeatedly administered until the pain is below a 1 of 10 on a visual analog scale (VAS). To effectively treat ecchymosis, the hydrophilic HASA-gel matrix may be repeatedly administered until removal of the composition does not result in pain. To effectively treat boils, the hydrophilic HASA-gel matrix may be administered until the boil either becomes resorbed or erupts. To effectively treat epistaxis, the hydrophilic HASA-gel matrix may be administered until all blood flow from the nose has stopped for at least 5 minutes. To effectively treat skin issues, such as blisters, impetigo, tinea, herpes zoster and herpes, the hydrophilic HASA-gel matrix may be administered until the skin is healed and shows no visible signs of disease or other problems. To treat external skin diseases, the hydrophilic HASA-gel matrix may be used daily until all signs of the ailment are gone, wherein the patient's hair stops falling out, the fistula, wart, anal fissure, ringworm or other ailment are completely gone.

For surgery or situations when the trauma is scheduled, increased effectiveness can be obtained by using or increasing the pre-application time before the injury is incurred when coupled with post-trauma application. For example, the inventor found an increased effectiveness when the pre-application time was increased from 2 min to 1 hour. Similar to the post injury application, the exact pre-application time will depend upon the severity of the trauma. Such a pre-application time can be determined upon consultation with the treating physician. During the drop tests, it was noticed anticdotally that the pain upon impact seemed to be significantly less for 1 hour pre-application, thus indicating that the pre-application may reduce the pain of the trauma. For example, pre-application time may be from about 1 minute to about 1 hour prior to the occurrence of tissue damage; more preferably, from about 1 minute to about 2 hours; more preferably from about 1 minute to about 4 hours; more preferably, from about 1 minute to about 6 hours; more preferably, from about 1 minute to about 12 hours; more preferably, from about 1 minute to about 24 hours; more preferably, from about 1 minute to about 48 hours; most preferably from about 1 minute to about 72 hours.

For chronic ailments or injuries, such as injuries to the ligament, tendon, bone, tissue, fistula, wart, anal fissure or ringworm, the hydrophilic HASA-gel matrix may be administered for one hour a day until the ailment is resolved. To effectively treat an injury to ligament, tendon or bone, the hydrophilic HASA-gel matrix may be administered for a few hours a day until the tissue is healed, as verified by MRI or X-ray.

Additionally, the method of the present invention is particularly useful for treating surgical injuries, including injuries incurred during, as a result of or in association with any surgical procedure, including removal or repair of circulatory, digestive, endocrine, lymphatic, integumentary, muscular, nervous, reproductive, respiratory, skeletal, urinary, sensory, or excretory systems. Exemplary surgical procedures may include abdominal surgery; abdominoplasty; adenoidectomy; amputation; angioplasty; appendicectomy; arthrodesis; arthroplasty; arthroscopy; biopsy; brain surgery; breast biopsy; cosmetic surgery, cauterization; cesarean section; cholecystectomy; circumcision; colon resection; colostomy; corneal transplantation; diverticulectomy; episiotomy; endarterectomy; fistulotomy; frenectomy; frontalis lift; fundectomy; gastrectomy; grafting; heart transplantation; hemorrhoidectomy; hepatectomy; hernia repair; hysterectomy; kidney transplantation; laminectomy; laparoscopy; laparotomy; laryngectomy; lumpectomy; lung transplantation; mammectomy; mammoplasty; mastectomy; mastoidectomy; nephrectomy; orchidectomy; pancreaticoduodenectomy; parathyroidectomy; prostatectomy; sigmoidostomy; sphincterotomy; splenectomy; thymectomy; thyroidectomy; tonsillectomy; tracheotomy; ulnar collateral ligament; reconstruction. Exemplary cosmetic surgical procedures, may include liposuction; liposculpture; rhinoplasty; rhytidectomy; blepharoplasty; sclerotherapy; vaginoplasty; phalloplasty; labiaplasty; abdominoplasty; chemical peels; surgical augmentations, implants or reductions, such as lip augmentation, chin augmentation or breast implants; mole removal; scar removal or repair; tattoo removal; skin resurfacing; dermabrasion; and collagen injections.

In another embodiment, the compositions and methods of the present invention is used to treat deep tissue wounds in any portion of body, such as the epithelial tissue, connective tissue, muscles, nervous tissue, organ, nerve, brain, arteriol, lymphatic, or bone. The method may also be used to treat any injury or wound of, including deep tissue wounds of, as well as any ailment of the circulatory, digestive, endocrine, lymphatic, integumentary, muscular, nervous, reproductive, respiratory skeletal, urinary, sensory, or excretory systems.

The aforementioned effective treatment of an ailment or injury is achieved by administering a hydrophilic HASA-gel matrix for an extended period of time sufficient to provide a beneficial effect. Generally, the longer the period of time in which the hydrophilic HASA-gel matrix is exposed to the site of tissue damage, the more effective the hydrophilic HASA-gel matrix will be in treating the tissue damage. This extended topical treatment period is a novel aspect of the present invention that has not been previously known to or recognized by the homeopathic community. Without wishing to be bound by theory, topically administering the HASA-gel matrix for an extended duration increases therapeutic effect.

The hydrophilic HASA-gel matrix can be administered intermittently or continuously for an extended period of time, including hours, days, or weeks, as needed, to any bodily surface in order to effectively treat an ailment or injury. For topical administrations to a bodily surface, treatments may involve the topical application of a high or medium potency HASA-gel matrix continuously for about 30 minutes or more or intermittently for a total of 2 hours or more in a 24 hour period. Alternatively, treatments may be continuously or intermittently topically applied for about 2 hours or more in a 24 hour period, more preferably, about 4 hours or more in a 24 hour period, even more preferably, about 8 hours or more in a 24 hour period, and most preferably, about 12 hours or more in a 24 hour period. In another embodiment, the treatment may be a continuous or intermittent topical application of a high potency hydrophilic HASA-gel matrix for about 24 hours or more, preferably, about 36 hours or more, more preferably, about 48 hours or more, and most preferably, about 60 hours or more. In yet another embodiment, the treatment duration may be about 2 to about 12 hours, preferably, about 4 to about 12 hours, more preferably, about 6 to about 12 hours, and most preferably about 8 to about 12 hours. With respect to the aforementioned embodiments directed to intermittent treatment, the hydrophilic HASA-gel matrix may be applied in intervals of about 30 minutes or more, preferably, about 1 hour or more, more preferably, about 2 hours or more and most preferably, about 4 hours or more.

Without wishing to be bound by any theory, it is believed that the hydrophilic HASA-gel matrix begins to produce therapeutic results immediately upon topical administration to a bodily surface of a vertebrate. Because concentrations of the homeopathic agent in the hydrophilic HASA-gel matrix required to become therapeutic are very small, it is expected that the product becomes therapeutic immediately.

The effective treatment of an ailment or injury is dependent upon the potency of the hydrophilic HASA-gel matrix, the duration of topical administration, and the topical application to a surface area over which the HASA-gel matrix is applied. Each of these parameters in turn is dependent on and affected by the severity of the ailment as well as the body chemistry and tolerance of an individual patient or subject. The more severe an ailment, the greater the potency, duration and/or applied surface area necessary to achieve effective treatment. In one embodiment, the method of the present invention may be tailored to the patient and injury to attain therapeutic effectiveness. Consequently, infinitesimally short application times and small application areas are effective, however, those skilled in the art would realize that these parameters should be increased to maximize the efficacy.

The following embodiments are provided as exemplary guidelines for treating various ailments and injuries using the compositions and methods of the present invention. A skilled homeopath may make adjustments to these parameters, as necessary, within the scope of the present invention. The hydrophilic HASA-gel matrix should keep the site of injury or ailment continuously moist and in direct contact with the hydrophilic HASA-gel matrix throughout the duration of the treatment. The hydrophilic HASA-gel matrix may be removed and reapplied as needed. To prevent evaporation, the hydrophilic HASA-gel matrix may be covered with Tegaderm.R® or another plastic covering. To facilitate and expedite healing, hydrophilic HASA-gel matrix is preferably applied to the site of injury or ailment as soon as possible after incurring the ailment or injury.

In one embodiment, the compositions and methods of the present invention involves the localized and topical administration of a hydrophilic HASA-gel matrix including one or more of the compositions or ingredients listed in Table 1 above, having potency of at least 6 C or a dilution factor of at least $10^{-4}$, to treat inflammation and maintaining the hydrophilic HASA-gel matrix in contact with an area of inflammation. The hydrophilic HASA-gel matrix is continuously administered until the acute inflammation phase is complete. The administration duration may be a continuous period of about 12 to about 48 hours. Subsequently, the hydrophilic HASA-gel matrix may be administered about 4 hours or more per day up to about 4 weeks until the sub-acute inflammation stage is complete.

In another embodiment, the compositions and methods of the present invention are used to treat a patient for tissue damage, pain and/or any injury, such as a surgical injury or trauma. The method involves topically administering a hydrophilic HASA-gel matrix to the site of tissue damage, pain, or surgical injury and maintaining the hydrophilic HASA-gel matrix in an aqueous environment in contact with the site for an extended period of time. The hydrophilic HASA-gel matrix may include *Arnica Montana, Bellis perennis, Calcarea phosphorica, Calendula, Hypericum perforatum, Ledum palustre, Rhus toxicodendron, Millefolium, Ruta graveolens, Symphytum officinale, Apis Mel, Cantharis, Urticartia Urens, Belladonna, Ferrum Metallicum, Staphasagria, Hepar Sulphuricum, Euphatorium perfoliatum, Bryonia, Naturm Sulphuricum, Calcarea carbonica, Hamamelis* or combinations thereof, and may be formulated to have a potency of about 10M. The hydrophilic HASA-gel matrix may be continuously administered until the acute phase is complete. Exemplary administration duration may be a continuous period of about 12 to about 48 hours. Subsequently, the hydrophilic HASA-gel matrix may be administered in a potency of about 1M up to about 2 to about 24 hours a day for a period of up to about 4 weeks until the sub-acute stage is complete.

In another embodiment, the compositions and methods of the present invention are used to effectively repair tissue damage or treat pain and/or inflammation of soft tissue. Specifically, the method may be used to treat a patient for any surgical injury; treat a tear or injury to a ligament and/or tendon, such as tendonitis or a tear or injury of the anterior cruciate ligament (ACL); or treat an acute trauma, such as ecchymosis, sprain, concussion, muscle tear or strain, to repair soft tissue, alleviate pain and/or alleviate inflammation. The method involves topically administering a hydrophilic HASA-gel matrix formulated to have a potency of about 10M locally to the site of injury or ailment and maintaining the hydrophilic HASA-gel matrix in an aqueous environment in contact with the site. In one embodiment, the hydrophilic HASA-gel matrix includes a mixture of one or more of *Arnica montana* and/or *Bellis perennis*. In an alternative embodiment, the hydrophilic HASA-gel matrix includes a mixture of one or more of *Arnica montana, Rhus toxicodendron, Ruta graveolens*, and/or *Ledum palustre*. The hydrophilic HASA-gel matrix may be applied until the acute phase is complete, preferably for a period of about 12 to about 48 hours. Subsequently, a 1 M potency of the hydrophilic HASA-gel matrix may be applied until the sub-acute phase is complete, preferably about 1 week or alternatively, up to about 4 weeks for about 2 to about 24 hours a day.

The methods of using the HASA hydrophilic homeopathic formulations of the present invention can also treat difficult and/or chronic ailments, such as Lyme disease pain, migraine headaches, etc., that are not normally considered topically treatable. Furthermore, the treatment may effectively stabilize the ailment or injury on a long term to permanent basis without embarrassing odors, redness, stains, greasiness; or unpleasant physical sensations such as stinging, itching, burning, cooling sensations, irritations, drying of skin, or numbness, found in many, if not most, currently known topical analgesics or anti-inflammatory agents.

In another embodiment, the compositions and methods of the present invention are used to effectively repair tissue damage or treat pain and inflammation resulting from damage of nerve tissue, such as damage to the nerves in the fingertips, toes, genitals, spine tailbone, and/or eyeball. The method may involve localized application of a hydrophilic HASA-gel matrix including *Hypericum* perforatum formulated at a potency of at least 6 C or a dilution factor of at least $10^{-4}$, and maintaining the hydrophilic HASA-gel matrix in an aqueous environment for an extended period of time to provide effective therapeutic treatment. In another embodiment, the hydrophilic HASA-gel matrix may be formulated in a potency of about 1M and applied until the pain is eliminated or relieved. The hydrophilic HASA-gel matrix may be reapplied as needed to treat any reoccurrence of pain.

In another embodiment, the compositions and methods of the present invention are used to effectively repair tissue so and/or improve or facilitate healing of a wound, including broken skin injuries, such as cuts or scrapes; burns, such as chemical burns, temperature burns, or sunburns; or surgical incisions. The method may involve formulating a hydrophilic HASA-gel matrix including one or more of *Calen-*

*dula, Urticaria Urens*, and/or *Staphasagria* having potency of at least 6 C or a dilution factor of at least $10^{-4}$. The hydrophilic HASA-gel matrix may be applied directly to and/or around the wound until the wound is healed.

In another embodiment, the compositions and methods of the present invention are used to effectively repair bone tissue, such as bone tissue damaged by bone fractures, bone bruises, or trauma to the ocular region. The method may involve local application of a hydrophilic HASA-gel matrix including one or more of *Symphytum officinale* and/or *Ruta graveonens* formulated in a potency of about 1M. The hydrophilic HASA-gel matrix may be topically applied for about 4 hours a day until the bone is healed.

In another embodiment, the compositions and methods of the present invention are used to effectively repair the tissue and/or treat pain and inflammation resulting from acute trauma to the head or scalp, such as would be incurred during a concussion. Alternatively, the hydrophilic HASA-gel matrix may be formulated in a potency of about 10M and applied until the acute phase is complete, preferably about 12 to about 48 hours. Subsequently, a 1 M hydrophilic HASA-gel matrix may be applied until the sub-acute phase is complete, preferably about up to about 4 weeks for about 2 to about 24 hours a day.

In another embodiment, the compositions and methods involves topical localized use of a hydrophilic HASA-gel matrix including one or more of the remedies listed in Table 2 having potency of at least 6 C or a dilution factor of at least $10^{-4}$ maintained in an aqueous environment for an extended amount of time for acute conditions. A 1 M of the indicated hydrophilic HASA-gel matrix should be applied continuously locally until the problem is resolved. The effects are cumulative, thus if it is not possible to use the HASA-gel matrix continuously, the therapeutic effectiveness may be reduced. The entire area should be covered for maximum efficacy, if possible.

In another embodiment, the compositions and methods of the present invention are used to effectively treat boils. The method involves locally applying to the boil a hydrophilic HASA-gel matrix including Hep and Sil in a potency of about 1M, and maintaining the hydrophilic HASA-gel matrix in an aqueous environment. The hydrophilic HASA-gel matrix may be continuously applied to the boil until it is resorbed or erupts.

In another embodiment, the compositions and methods comprises topical localized use of a hydrophilic HASA-gel matrix including one or more of the remedies listed above in Table 3 having potency of at least 6 C or a dilution factor of at least $10^{-4}$ in an aqueous environment for an extended amount of time for chronic ailments. A 1 M potency of the indicated homeopathic compound should be applied locally for 4 to 8 hours a day until the problem is resolved. The entire injured area should be covered for maximum efficacy, if possible.

In yet another embodiment, the compositions and methods of the present invention are used to effectively treat eczema or ringworm. The method involves locally applying a hydrophilic HASA-gel matrix as indicated above in Table 3 to the site of the ailment in an aqueous environment. The hydrophilic HASA-gel matrix may be topically administered until eruption, preferably about 4 to about 8 hours per day. The invention may be reapplied as necessary.

In another embodiment, the compositions and methods of the present invention are used to effectively treat hemorrhoids, fistulas or rectal fissures by locally applying a hydrophilic HASA-gel matrix as indicated above in Table 3, and maintaining the hydrophilic HASA-gel matrix in an aqueous environment. The hydrophilic HASA-gel matrix may be applied to and cover an area around the anus. In an alternative embodiment, the composition may be formulated as a suppository which is released over an extended period of time, preferably over a period of about 4 to 8 hours.

In another embodiment, the compositions and methods are used to treat strains, tears or other injuries to ligaments, such as the ligament of a knee. Upon application of the hydrophilic HASA-gel matrix having potency of at least 6 C or a dilution factor of at least $10^{-4}$, including but not limited to $10^{-000000000}$, the ligament will be effectively treated without requiring any or minimal surgical correction. To expedite healing, the knee may be kept in a straight leg brace to prevent bending. Optionally, the hydrophilic HASA-gel matrix may be inserted within the brace.

In yet another embodiment, the compositions and methods are used to treat blunt trauma to deep muscle tissue. The method involves topical application of a high potency hydrophilic HASA-gel matrix including *Bellis Perennis* and *Arnica* having potency of at least 6 C or a dilution factor of at least $10^{-4}$, preferably 10M, to the skin for a period of about 8 hours. The hydrophilic HASA-gel matrix is effective for eliminating pain and inflammation of minor traumas and preventing ecchymosis associated with deep muscle bruises.

In yet another embodiment, the compositions and methods are used to treat minor abrasions. The method involves topical application of the hydrophilic HASA-gel matrix including *calendula* formulated at a potency of at least 6 C or a dilution factor of at least $10^{-4}$ to the minor abrasions for a period of about 4 hours a day. The hydrophilic HASA-gel matrix is applied to the area around the wound and may expedite the rate of healing by about 40%.

In yet another embodiment, the compositions and methods are used to treat sunburns or minor burns. The method involves topical application of a hydrophilic HASA-gel matrix including *calendula* formulated at a potency of at least 6 C or a dilution factor of at least $10^{-4}$ to the minor abrasions for a period of about 4 hours a day. The hydrophilic HASA-gel matrix is applied to the area around the wound and may expedite the rate of healing by about 40%.

In yet another embodiment, the compositions and methods are used to treat bone fractures. The method involves topical application of a hydrophilic HASA-gel matrix including *Symphytum* and calc phos, or alternatively *staphasagria* formulated at a potency of at least 6 C or a dilution factor of at least $10^{-4}$ to the skin surrounding a broken bone or fractured bone. The treatment may substantially increase the fracture healing rate.

In yet another embodiment, the compositions and methods are used to treat surgical incision injuries. The method involves topical application of a hydrophilic HASA-gel matrix including *staphasagria* at a potency of at least 6 C or a dilution factor of at least $10^{-4}$ to the area around an incision for a period of about 4 hours a day. The treatment may substantially increase the healing rate by about 30%.

In still yet another embodiment, the compositions and methods are used to treat a cyst or boil that is sensitive to the touch. The method involves topical application of a hydrophilic HASA-gel matrix including *Staphasagria, silicea*, or *hepar* sulph as one skilled in the art of homeopathy would choose in a potency of at least 6 C or a dilution factor of at least $10^{-4}$ to the cyst or boil until it erupts or becomes resorbed over a period of about 24 hours.

The hydrophilic HASA-gel matrix of present invention offers numerous advantages and unexpected benefits. Specifically, the remedies of the present invention are effective for treating an ailment or injury, particularly a localized ailment or injury, when administered in accordance with the method of the present invention. The method substantially prevents, reduces the severity of, improves the condition of, expedites the healing of, cures, or combinations thereof any ailment or injury, including severe ailments or injuries. In addition, the methods of the present invention offer rapid and effective treatment without incurring harmful side effects. For example, relief from pain, inflammation, infection, or any symptom or condition of the ailment or injury may occur within about 30 seconds to about 2½ minutes from the first topical application of the high potency hydrophilic HASA-gel matrix of the present invention. Additionally, the therapeutic treatment may last for over 8 hours after application.

Another aspect of the current invention comprises a method for preventing or reducing tissue damage comprising the step of contacting the biological tissue of an animal in need of such prevention or reduction with the hydrophilic HASA-gel matrix, wherein the HASA comprises a combination of a homeopathic compound having a potency of at least 6 C or a dilution factor of at least $10^{-4}$ and an uninhibited aqueous composition. The tissue damage may include scarring, bruising, tissue discoloration, tissue necrosis, and inflammation, and may be the result of any anticipated tissue trauma, including, but not limited to surgical procedures. It is further noted that the animal may include, but is not limited to humans, dogs, goats, horses, cats, cows, chickens, rabbits, hares, wolves, mice, rats, sheep, pigs, foxes, and non-human primates, as well as any reptile or bird species. Additionally, the HASA may be in contact with the biological tissue for a period ranging from approximately seconds to approximately weeks prior to the anticipated tissue trauma. In one embodiment, the hydrophilic HASA-gel matrix is contacted with the biological tissue from about 1 minute to about 72 hours prior to the occurrence of tissue damage. In another embodiment, the hydrophilic HASA-gel matrix is contacted with the biological tissue from about 1 minute to about 48 hours prior to the occurrence of tissue damage.

At the time the hydrophilic HASA-gel matrix of the present invention is topically applied to a bodily surface, the HASA-gel matrix is hydrated such it contains a sufficient amount of HASA to maintain the HASA-gel matrix in an aqueous environment for a sufficient period of time to achieve a therapeutic effect.

8. Agent Delivery Device

In yet another embodiment, the present invention relates to a homeopathic agent delivery device. The device includes a sheet of a porous hydrophilic polymer and HASA within the sheet. The HASA includes a homeopathic compound at a potency of at least 6 C or a dilution factor of at least $10^{-4}$ and an uninhibited aqueous composition.

The device may be used in a method for preventing or reducing tissue damage, the method including contacting a biological tissue of an animal in need of such prevention or reduction with the delivery device.

The device may also be used in a method of treating ligament damage in a patient's knee including contacting the knee with the delivery device, wherein no surgical procedures are required to repair the ligament damage. Preferably, the method further includes having the patient wear a straight leg brace to prevent bending.

9. HASA and Hydrophilic Gel Compositions

In one alternative embodiment, a gel base may be mixed with a minimum of 41% HASA. It is recommended that as much HASA as possible be mixed with the gel. This HASA gel may be dabbed on the skin and quickly absorbed, however, the therapeutic effectiveness will be increased by placing it on the skin in a manner that does not allow it to be absorbed such as applying it to a gauze pad soaked in HASA gel such that it does not dry out until the end of the recommended therapy duration.

In another alternative embodiment, the hydrophilic gelling agents are first cross-linked to form a gel matrix, such as hydrogel carrier prior to being combined with the HASA. The hydrogel may be exposed to the HASA for a sufficient period of time prior to the topical application of the HASA within the gel matrix. Preferably, these components are exposed and allowed to be combined with one another for at least about 5 minutes, more preferably, for at least about 1 hour, and most preferably, for about 1 to about 3 hours. The exact exposure time will depend on the temperature, hydrophilic and/or hydrophobic characteristics of the hydrogel polymers as well as other variables. However, a minimum of 41% HASA should be absorbed.

As mentioned above, a gel base may be mixed with a minimum of 41% HASA. The percentages of HASA are by weight of the composition, unless stated otherwise. In another embodiment, a gel base may be mixed with a minimum of 45% HASA; a minimum of 50% HASA; a minimum of 55% HASA; a minimum of 60% HASA; a minimum of 65% HASA; a minimum of 70% HASA; a minimum of 75% HASA; a minimum of 80% HASA; a minimum of 85% HASA; a minimum of 90% HASA; a minimum of 95% HASA; or a minimum of 99% HASA.

The HASA gel may include 1-59% gel; more preferably, 1-55% gel; more preferably, 1-50% gel; more preferably, 1-45% gel; more preferably 1-40% gel; more preferably 1-35% gel; more preferably, 1-30% gel; more preferably 1-25% gel; and more preferably 1-20% gel, where the percentages are weight to weight of the composition, unless stated otherwise.

Preferably, the HASA gel is administered according to the methods described for the hydrophilic HASA-gel matrix.

Preferably, the HASA gel is used to treat the injuries and alignments described in connection with the hydrophilic-gel matrix above.

The following examples are included to demonstrate certain embodiments of the invention. Those of skill in the art should, however, in light of the present disclosure, appreciate that modifications can be made in the specific embodiments that are disclosed and still obtain a like or similar result without departing from the spirit and scope of the invention. Therefore, the examples are to be interpreted as illustrative and not in a limiting sense.

EXAMPLES

Note: For all drop tests, *Arnica* is the only homeopathic compound that is being evaluated since it is the only homeopathic compound that affects bruising to soft tissue. Thus, even when other homeopathic compounds are included, only *Arnica* is evaluated.

Also, where not specified, the water used for the examples was common tap water or spring water. Drop tests were conducted using a 3 lb bar that was dropped through a paper tube from either 20" (half drop) or 30" (full drop). The impact area was then monitored over the course of several days with photographs taken on each day, in most but not all cases, to document the discoloration. The bruises were then rated on a scale from 0-10 from the photographs by 2 or more evaluators.

Comparison of Effective Treatment and Placebo:

The bruising ratings for our reference standard of HASA soaked paper towel (PT&W) were significantly higher than for the no treatment or placebo for both the 20 inch drops and the 30 inch drops. For the 20 inch drop, the mean rating of the paper towel soaked in HASA technique is a 1.33 while the placebo was a 5.50. For the 30 inch drop, the mean rating of the paper towel soaked in HASA technique is a 3.50 while the placebo or no treatment was a 6.67. The data is shown in Table 5.

Comparison of Effective Treatment, Ineffective Treatment, Ineffective Treatment, and Placebo/No Treatment These standards were used to evaluate various manufacturing techniques for hydrogel. Techniques that had a low bruising rating were deemed effective and those that had high bruising ratings were deemed ineffective. For the 20 inch drop techniques deemed effective, the average rating was 0.70 while the ineffective treatment rating was 5.33 compared to 1.33 and 5.50 for the HASA soaked paper towel and placebo/no treatment, respectively. The data is shown in Table 5.

TABLE 5

Summary Table-Data from All Drop Tests

| Test Description | Eg. | Drop Size | Rating | Mean | SD |
|---|---|---|---|---|---|
| Effective Half PT&W | 5 | Half | 0 | 1.33 | 1.21 |
| | 3 | Half | 1 | | |
| | 3 | Half | 2 | | |
| | 28 | Half | 0 | | |
| | 23 | Half | 3 | | |
| | 4 | Half | 2 | | |
| Effective Half Hydrogel | 7 | Half | 0 | 0.70 | 0.95 |
| | 8 | Half | 0 | | |
| | 24 | Half | 1 | | |
| | 25 | Half | 3 | | |
| | 25 | Half | 1 | | |
| | 25 | Half | 0 | | |
| | 25 | Half | 1 | | |
| | 25 | Half | 1 | | |
| | 25 | Half | 0 | | |
| | 34 | Half | 0 | | |
| Placebo Half | 20 | Half | 8 | 5.50 | 2.65 |
| | 20 | Half | 2 | | |
| | 20 | Half | 7 | | |
| | 20 | Half | 5 | | |
| Ineffective Half Hydrogel | 16 | Half | 5 | 5.33 | 0.82 |
| | 15 | Half | 7 | | |
| | 17 | Half | 5 | | |
| | 18 | Half | 5 | | |
| | 10 | Half | 5 | | |
| | 10 | Half | 5 | | |
| Effective Full | 6 | Full | 3 | 3.50 | 0.71 |
| | 9 | Full | 4 | | |
| Placebo Full | 21 | Full | 6 | 6.67 | 2.08 |
| | 21 | Full | 5 | | |
| | 22 | Full | 9 | | |
| Ineffective Full Hydrogel | 13 | Full | 10 | 8.83 | 1.60 |
| | 14 | Full | 8 | | |
| | 14 | Full | 6 | | |
| | 19 | Full | 10 | | |
| | 11 | Full | 10 | | |
| | 12 | Full | 9 | | |

T-Test Comparisons of Different Groups for ½ Drop Tests:

The data shown for half drops in Table 5 was used to perform T-tests on various combinations of applications to determine the statistical difference between each comparison. The Effective paper towel and water tests were compared to the Effective hydrogel tests resulting in a P value of 0.2623 which indicates that they were not statistically different.

Several other comparisons were performed. In each case, the Effective Hydrogel or HASA paper towel and water applications were determined to be extremely statistically different than the placebo or Ineffective hydrogel. In three cases the P value was 0.0001 while two cases having a P value was 0.0002 and 0.009. A summary of all the T-tests that were performed is shown in Table 6 below.

TABLE 6

T-Tests on Half drops
The ratings from the drop tests done at 20 inches (half) were used to perform t-tests between the placebo/no treatment and treatments that worked (effective) and those that did not work (ineffective).

| Test Group 1 | Test Group 2 | P Value | Result |
|---|---|---|---|
| Effective PT&W | Effective Hydrogel | 0.2623 | Not Statistically different |
| Effective Hydrogel | Placebo | 0.0002 | Statistically different |
| Effective Hydrogel | Ineffective Hydrogel | 0.0001 | Statistically different |
| Effective | Placebo | 0.0001 | Statistically different |
| Effective PT&W | Placebo | 0.0090 | Statistically different |
| Effective PT&W | Ineffective Hydrogel | 0.0001 | Statistically different |

HASA does not Form in the Presence of Hydrophilic Substance:

A number of samples were tested where we attempted to mix the pellets into the water which was held in a hydrogel ("post-load"). A small amount of HASA<10% (estimated) was added to the hydrogel by soaking or other methods. The hydrogels were often 90% water and it was expected that they would readily absorb the remedy and become propagated similar to the way it occurs with a glass of water; however, in each case it was not possible to detect that the HASA formed and all post-loaded tests failed as shown in Table 7. A number of different variations were attempted, hydrogel placed on pellets, hydrogel placed on a thin film of HASA, and varying the length of time after the hydrogel came in contact with the homeopathic remedy. None of these cases worked.

In comparison, anecdotal results of bruises where a hydrogel was soaked in a HASA for 3 hours worked fine. Hydrogels are known to absorb 3× their weight and it is estimated that they absorbed more than 41% HASA. In these cases it appears to work, as long as the HASA is formed prior to the contact with the gel. Unfortunately, the evaluation of the 3 hour soaked hydrogel was completed by kicking a leg against a table and was not documented.

TABLE 7

Demonstrates that water exposed to hydrophilic substance will not form HASA

| Example | Gel Treatment | Drop Size | Rating[+]. |
|---|---|---|---|
| 15 | Post-loaded | 20" | Fail |
| 17[$] | Post-loaded | 20" | Fail |
| 18[$] | Post-loaded | 20" | Fail |
| 19 | Post-loaded | 30" | Fail |
| 13 | Post-loaded | 30" | Fail |
| 14 | Post-loaded | 30" | Fail |
| 14 | Post-loaded | 30" | Fail |
| 7 | Pre-loaded | 20" | Pass |
| 8 | Pre-loaded | 20" | Pass |
| 25 | Pre-loaded | 20" | Pass |
| 25 | Pre-loaded | 20" | Pass |
| 25 | Pre-loaded | 20" | Pass |
| 25 | Pre-loaded | 20" | Pass |
| 25 | Pre-loaded | 20" | Pass |

TABLE 7-continued

Demonstrates that water exposed to hydrophilic substance will not form HASA

| Example | Gel Treatment | Drop Size | Rating+ |
|---------|---------------|-----------|---------|
| 25 | Pre-loaded | 20" | Pass |
| 9 | Pre-loaded | 30" | Pass |

$Estimated based on notes that bad bruises had developed. No photographs were taken.
+The ratings were done on a pass/fail basis due to the different criteria used for 20" drops and 30" drops. For 20" drop tests, the presence of a purple bruise (Rating of 5) was considered a failure. For 30" drop tests, a ratings ≤4 were a pass and ratings ≥6 were a failure.

Significance of Pre-Application Length:

The effect of the length of pre-application of the HASA was evaluated by comparing pre-application times of less than two minutes to 1 hour for cases where the amount of pressure was controlled. The bruises that developed were photographed and rated on a scale from 0 to 10, increasing in severity. A purple bruise is rated at least a 5, if not higher. The mean rating of the tests with a pre-application time of less than 2 minutes was 6.5, whereas the mean rating of the tests with pre-application time of 1 hour was 0.88. The notable difference in the mean values for the two experiments indicates that the length of pre-application is crucial to prevent bruising. The data is shown in Table 8 below:

TABLE 8

Demonstrates the effect of pre-application time Pre-application of the arnica product prior to the impact significantly affected the results. All were applied for approximately the same time after the impact.

| Example | Pre-app time | Rating | Mean | SD |
|---------|--------------|--------|------|-----|
| 1 | <2 mins | 8 | 6.5 | 2.12 |
| 2 | <2 mins | 5 | | |
| 7 | ~1 hour | 0 | 0.88 | 0.99 |
| 24 | ~1 hour | 1 | | |
| 25 | ~1 hour | 3 | | |
| 25 | ~1 hour | 1 | | |
| 25 | ~1 hour | 0 | | |
| 25 | ~1 hour | 1 | | |
| 25 | ~1 hour | 1 | | |
| 25 | ~1 hour | 0 | | |

The Significance of Electron Beam or U.V. Curing

In multiple cases we observed where energy resulted in the destruction of the HASA, presumably due to electron beam or U.V. curing indicated by an ineffective gel. All of the cases where the product was manufactured where it did not get exposed to greater than 121° F. or any other energy source such as e-beam or U.V. curing passed. However, some of the cases that were exposed to these radiation sources passed and others did not. The examples are listed in the table 9 below:

TABLE 9

Demonstrates the effect electron beam or U.V. curing Pre-application of the arnica product prior to the impact significantly affected the results. All were applied for approximately the same time after the impact.

| | PASS (Eg) | FAIL (Eg) |
|---|-----------|-----------|
| Not exposed to U.V. or e-beam | 24, 34 | None |
| Exposed to U.V. or e-beam | 7, 8, 9, 25 | 10, 11, 12, 13, 14, 26 |

Paper Towel & Water—Less than 2 Mins

Example 1

CF&E 50M PT&W; Rating: 3, 8

The effectiveness of HASA applied with a paper towel to treat trauma incurred by dropping a breaker bar onto the hip of human test subject was studied. HASA was synthesized by combining 1 gram of 50M *Arnica, Ruta,* and *Ledum* lactose/sucrose pellets per 8 ounces of water, and stirred vigorously. The homeopathic remedies were manufactured by Washington Homeopathic Products, Inc.

Prior to incurring any trauma, a 2×4 inch paper towel soaked with HASA was topically applied to the hip region of the test subject for less than 2 minutes. Subsequently, a 3 lb, 1 inch diameter breaker bar was dropped through a 2 inch diameter, 20 inch long paper tube that was held perpendicular to the body of the human test subject and onto the test subject's hip. The paper towel soaked in HASA was again topically applied to the test subject's hip and covered by Glad's Press-N-Seal™ Saran wrap for about 17 hours after the breaker bar was dropped. There was no control for pressure. This experiment was performed on two different occasions and at two different locations on the hip region. The bruises that developed were rated a 3 and an 8 on a scale from 0 to 10, increasing in severity. The mean rating is a 5.50.+−0.3.54.

Example 2

Boiron 50M ARL PT&W. Rating: 0

The effectiveness of HASA applied with a paper towel to treat trauma incurred by dropping a breaker bar onto the hip of human test subject was studied. HASA was synthesized by combining 1 gram of 50M *Arnica, Ruta,* and *Ledum* lactose/sucrose pellets per 8 ounces of water, and mixed vigorously. Extra 50M *Arnica* was added to be certain that HASA indeed contained *Arnica*. The homeopathic remedies were manufactured by Boiron®.

Prior to incurring any trauma, a 2×4 inch paper towel soaked with HASA was topically applied to the hip region of the test subject for less than 2 minutes. Subsequently, a 3 lb, 1 inch diameter breaker bar was dropped through a 2 inch diameter, 20 inch long paper tube that was held perpendicular to the body of the human test subject and onto the test subject's hip. The paper towel soaked in HASA was again topically applied to the test subject's hip and covered by Glad's Press-N-Seal™ saran wrap for about 17 hours after the breaker bar was dropped. No pressure was applied. The bruise that developed was rated a 5 on a scale from 0 to 10, increasing in severity.

Paper Towel & Water—20 Mins

Example 3

CF&E 50M PT&W (AquaMed Technologies Inc. & New Mix). Rating: 1.2

The effectiveness of HASA applied with a paper towel to treat trauma incurred by dropping a breaker bar onto the hip of human test subject was studied. The HASA was synthesized by combining 1 gram of 50M *Arnica, Ruta,* and *Ledum* lactose/sucrose pellets per 8 ounces of water, and stirred vigorously. The homeopathic remedies were manufactured by Washington Homeopathic Products, Inc.

Prior to incurring any trauma, a 2×4 inch paper towel soaked with HASA was topically applied to the hip region of the test subject for about 20 minutes. Subsequently, a 3 lb, 1 inch diameter breaker bar was dropped through a 2 inch diameter, 20 inch long paper tube that was held perpendicular to the body of the human test subject and onto the test subject's hip. The paper towel soaked in HASA was again topically applied to the test subject's hip and covered by Glad's Press-N-Seal™ saran wrap for about 18 hours after the breaker bar was dropped. This experiment was performed on two different occasions and at two different locations on the hip region. No pressure was applied. The bruises that developed were rated a 1 and a 2 on a scale from 0 to 10, increasing in severity. The mean rating is a 1.50.+−0.0.71.

Example 4

Boiron 50M ARL PT&W; Rating: 2

The effectiveness of HASA applied with a paper towel to treat trauma incurred by dropping a breaker bar onto the hip of human test subject was studied. The HASA was synthesized by combining 1 gram of 50M *Arnica, Ruta*, and *Ledum* lactose/sucrose pellets per 8 ounces of water, and mixed excessively. Extra 50M *Arnica* was added to be certain that HASA indeed contained *Arnica*. The homeopathic remedies were manufactured by Boiron®.

Prior to incurring any trauma, a 2×4 inch paper towel soaked with HASA was topically applied to the hip region of the test subject for about 20 minutes. Subsequently, a 3 lb, 1 inch diameter breaker bar was dropped through a 2 inch diameter, 20 inch long paper tube that was held perpendicular to the body of the human test subject and onto the test subject's hip. The paper towel soaked in HASA was again topically applied to the test subject's hip and covered by Glad's Press-N-Seal™ saran wrap for about 18 hours after the breaker bar was dropped. No pressure was applied. The bruise that developed was rated a 2 on a scale from 0 to 10, increasing in severity.

Paper Towel & Water

Example 5

CF&E 50M PT&W; Rating: 0

The effectiveness of HASA applied with a paper towel to treat trauma incurred by dropping a breaker bar onto the hip of human test subject was studied. HASA was synthesized by combining 1 gram of 50M *Arnica, Ruta*, and *Ledum* lactose/sucrose pellets per 8 ounces of water. The homeopathic remedies were manufactured by Washington Homeopathic Products, Inc.

Prior to incurring any trauma, a 2×4 inch paper towel soaked with HASA was topically applied to the hip region of the test subject. Subsequently, a 3 lb, 1 inch diameter breaker bar was dropped through a 2 inch diameter, 20 inch long paper tube that was held perpendicular to the body of the human test subject and onto the test subject's hip. The paper towel soaked in HASA was again topically applied to the test subject's hip and covered by Glad's Press-N-Seal™ saran wrap. There was no control for pressure. The bruise that developed was rated a 0 on a scale from 0 to 10, increasing in severity.

Paper Towel & Water—10 Mins

Example 6

Arnica 50M PT&W; Rating: 3 (Full Drop)

The effectiveness of HASA applied with a paper towel to treat trauma incurred by dropping a breaker bar onto the hip of human test subject was studied. HASA was synthesized by combining 1 gram of 50M *Arnica* lactose/sucrose pellets per 8 ounces of water. The 50M Arnica was manufactured by Boiron®.

Prior to incurring any trauma, a 2×4 inch paper towel soaked with HASA was topically applied to the hip region of the test subject for approximately 10 minutes. Subsequently, a 3 lb, 1 inch diameter breaker bar was dropped through a 2 inch diameter, 30 inch long paper tube that was held perpendicular to the body of the human test subject and onto the test subject's hip. The paper towel soaked in HASA was again topically applied to the test subject's hip and covered by Glad's Press-N-Seal™ saran wrap for about 12 hours after the breaker bar was dropped. There was no control for pressure. The bruise that developed was rated a 3 on a scale from 0 to 10, increasing in severity.

Pre-Loaded Hydrogel—1 hr

Example 7

Arnica 50M Pre-Loaded Hydrogel Sample Made by AquaMed Technologies Inc.; Rating: 0

The effectiveness of a HASA hydrogel composition to treat trauma incurred by dropping a breaker bar onto the hip of human test subject was studied. The HASA hydrogel composition was synthesized as a film by producing HASA by placing 8.2 grams of medicated 50M *Arnica* lactose/sucrose pellets per 1 gallon of water and stirred. 94% HASA was then combined with a hydrophilic gelling agent mixture supplied by AquaMed Technologies Inc. This HASA and hydrophilic gelling agent mixture was subsequently cross-linked with electron beam (e-beam) radiation using a Radiation Dynamics Inc. Dynamitron Mod. 1500-40. The resultant HASA hydrogel composition comprised about 94% by weight water all of which was from the HASA mixture. The number assigned to the production lot was # B110107-3. The 50M *Arnica* was manufactured by Boiron®.

Prior to incurring any trauma, a 2×4 inch HASA hydrogel composition was topically applied to the hip region of the test subject for about 1 hour. Subsequently, a 3 lb, 1 inch diameter breaker bar was dropped through a 2 inch diameter, 20 inch long paper tube that was held perpendicular to the body of the human test subject and onto the test subject's hip. The HASA hydrogel composition was again topically applied to the test subject's hip and covered by Glad's Press-N-Seal™ saran wrap for about 15 hours after the breaker bar was dropped. No pressure was applied. The bruise that developed was rated a 0 on a scale from 0 to 10, increasing in severity.

Pre-Loaded Hydrogel

Example 8

*Arnica* 50M Product Made for the HA Study by AquaMed Technologies Inc.; Rating: 0

The effectiveness of a HASA hydrogel composition to treat trauma incurred by dropping a breaker bar onto the hip of human test subject was studied. The HASA hydrogel composition was synthesized as a film by producing HASA by placing 8.2 grams of medicated 50M *Arnica* lactose/sucrose pellets per 1 gallon of water and stirred. 94% HASA was then combined with a hydrophilic gelling agent mixture supplied by AquaMed Technologies Inc. This HASA and hydrophilic gelling agent mixture was subsequently cross-linked with electron beam (e-beam) radiation using a Radiation Dynamics Inc. Dynamitron Mod. 1500-40. The resultant HASA hydrogel composition comprised about 94% by weight water, all of which was from the HASA mixture. The number assigned to the production lot was # B100708-3. The 50M *Arnica* was manufactured by Washington Homeopathic Products Inc.

Prior to incurring any trauma, a 2×4 inch hydrogel based homeopathic film was topically applied to the hip region of the test subject for approximately 2 minutes. Subsequently, a 3 lb, 1 inch diameter breaker bar was dropped through a 2 inch diameter, 20 inch long paper tube that was held perpendicular to the body of the human test subject and onto the test subject's hip. The HASA hydrogel composition was again topically applied to the test subject's hip and covered by Glad's Press-N-Seal™ saran wrap for about 18 hours after the breaker bar was dropped. There was no control for pressure. The bruise that developed was rated a 0 on a scale from 0 to 10, increasing in severity.

Example 9

Arnica (Cearna Face) 50M AquaMed Hydrogel Drop; Rating: 4 (Full Drop)

The effectiveness of a HASA hydrogel composition to treat trauma incurred by dropping a breaker bar onto the hip of human test subject was studied. The HASA hydrogel composition was synthesized as a film by producing HASA by placing 8.2 grams of medicated 50M *Arnica* lactose/sucrose pellets per 1 gallon of water and stirred. 94% HASA was then combined with a hydrophilic gelling agent supplied by AquaMed Technologies Inc. This HASA and hydrophilic gelling agent mixture was subsequently cross-linked with electron beam (e-beam) radiation using a Radiation Dynamics Inc. Dynamitron Mod. 1500-40. The resultant HASA hydrogel composition comprised about 94% by weight water, all of which was from the HASA mixture. The number assigned to the production lot was # B100412-3. The 50M *Arnica* was manufactured by Washington Homeopathic Products, Inc.

Prior to incurring any trauma, a 2×4 inch HASA hydrogel composition was topically applied to the hip region of the test subject for approximately 10 minutes. Subsequently, a 3 lb, 1 inch diameter breaker bar was dropped through a 2 inch diameter, 30 inch long paper tube that was held perpendicular to the body of the human test subject and onto the test subject's hip. The HASA hydrogel composition was again topically applied to the test subject's hip and covered by Glad's Press-N-Seal™ saran wrap for about 12 hours after the breaker bar was dropped. There was no control for pressure. The bruise that developed was rated a 4 on a scale from 0 to 10, increasing in severity.

Pre-Loaded Hydrogel Hr

Example 10

Arnica 50M Pre-Loaded by AquaMed Technologies Inc.; Rating 5, 5

The effectiveness of a HASA hydrogel composition to treat trauma incurred by dropping a breaker bar onto the hip of human test subject was studied. The HASA hydrogel composition was synthesized as a film by producing HASA by placing 8.2 grams of medicated 50M *Arnica* lactose/sucrose pellets per 1 gallon of water and stirred. 94% HASA was then combined with a hydrophilic gelling agent mixture supplied by AquaMed Technologies Inc. This HASA and hydrophilic gelling agent mixture was subsequently cross-linked with electron beam (e-beam) radiation using a Radiation Dynamics Inc. Dynamitron Mod. 1500-40. The resultant HASA hydrogel composition comprised about 94% by weight water, all of which was from the HASA mixture. The number assigned to the production lot was # R27726. The 50M *Arnica* was manufactured by Boiron®.

Prior to incurring any trauma, a 2×4 inch HASA hydrogel was topically applied to the hip region of the test subject for about 1 hour. Subsequently, a 3 lb, 1 inch diameter breaker bar was dropped through a 2 inch diameter, 20 inch long paper tube that was held perpendicular to the body of the human test subject and onto the test subject's hip. The HASA hydrogel composition was again topically applied to the test subject's hip and covered by Glad's Press-N-Seal™ saran wrap for about 15 hours after the breaker bar was dropped. This experiment was performed on two different occasions and at two different locations on the hip region. No pressure was applied. The bruises that developed were both rated a 5 on a scale from 0 to 10, increasing in severity. The mean rating is a 5.00.

Pre-Loaded Remedy D

Example 11

Remedy D Made by AquaMed Technologies Inc. for 4.1 Study; Rating: 10 (Full Drop)

The effectiveness of a HASA hydrogel composition to treat trauma incurred by dropping a breaker bar onto the hip of human test subject was studied. The HASA hydrogel composition was synthesized as a film by producing HASA by placing 8.2 grams of medicated 50M *Arnica, Ruta*, and *Ledum* lactose/sucrose pellets per 1 gallon of water and stirred. 94% HASA was then combined with a hydrophilic gelling agent mixture supplied by AquaMed Technologies Inc. This HASA and hydrophilic gelling agent mixture was subsequently cross-linked with electron beam (e-beam) radiation using a Radiation Dynamics Inc. Dynamitron Mod. 1500-40. The resultant HASA hydrogel composition comprised about 94% by weight water, all of which was from the HASA mixture. The number assigned to the production lot was # L101101. The homeopathic remedies were manufactured by Washington Homeopathic Products, Inc.

Prior to incurring any trauma, a 2×4 inch HASA hydrogel composition was topically applied to the hip region of the test subject for approximately 10 minutes. Subsequently, a 3 lb, 1 inch diameter breaker bar was dropped through a 2 inch diameter, 30 inch long paper tube that was held perpendicular to the body of the human test subject and onto the test subject's hip. The HASA hydrogel composition was again topically applied to the test subject's hip and covered by Glad's Press-N-Seal™ saran wrap for about 12 hours after the breaker bar was dropped. There was no control for pressure. The bruise that developed was rated a 10 on a scale from 0 to 10, increasing in severity.

Example 12

Remedy D Made by AquaMed Technologies Inc. For 4.1 Study; Rating: 9 (Full Drop)

The effectiveness of a HASA hydrogel composition to treat trauma incurred by dropping a breaker bar onto the hip of human test subject was studied. The HASA hydrogel composition was synthesized as a film by producing HASA by placing 8.2 grams of medicated 50M *Arnica, Ruta*, and Ledum lactose/sucrose pellets per 1 gallon of water and stirred. 94% HASA was then combined with a hydrophilic gelling agent mixture supplied by AquaMed Technologies Inc. This HASA and hydrophilic gelling agent mixture was subsequently cross-linked with electron beam (e-beam) radiation using a Radiation Dynamics Inc. Dynamitron Mod. 1500-40. The resultant HASA hydrogel composition comprised about 94% by weight water, all of which was from the HASA mixture. The number assigned to the production lot was # L101101. The homeopathic remedies were manufactured by Washington Homeopathic Products, Inc.

Prior to incurring any trauma, a 2×4 inch HASA hydrogel composition was topically applied to the hip region of the test subject for approximately 30 minutes. Subsequently, a 3 lb, 1 inch diameter breaker bar was dropped through a 2 inch diameter, 30 inch long paper tube that was held perpendicular to the body of the human test subject and onto the test subject's hip. The HASA hydrogel composition was again topically applied to the test subject's hip and covered by Glad's Press-N-Seal™ saran wrap for about 12 hours after the breaker bar was dropped. There was no control for pressure. The bruise that developed was rated a 9 on a scale from 0 to 10, increasing in severity.

Pre-Loaded UV Hydrogel

Example 13

90% Water UV Hydrogel Alone (Pre-Loaded); Rating: 10 (Full Drop)

The effectiveness of a 2×4 inch UV hydrogel pre-loaded with 90% HASA to treat trauma incurred by dropping a breaker bar onto the hip of human test subject was studied. The HASA hydrogel composition was synthesized by producing HASA by combining 50M Arnica lactose/sucrose pellets to produce 0.02% *Arnica* pellets in water. This HASA was then combined with a mixture of hydrophilic gelling agents supplied by R&D Medical Products Inc. This mixture was subsequently cross-linked with UV radiation to produce a hydrogel that was about 90% by weight water. The UV crosslinking ramped up to 170° F. for a few seconds. The number assigned to the production lot was #0819A10. The 50M Amica was manufactured by Washington Homeopathic Products, Inc.

Prior to incurring any trauma, the hydrogel film post-loaded with HASA was topically applied to the hip region of the test subject for about 10 minutes. Subsequently, a 3 lb, 1 inch diameter breaker bar was dropped through a 2 inch diameter, 30 inch long paper tube that was held perpendicular to the body of the human test subject and onto the test subject's hip. The UV hydrogel film post-loaded with 90% HASA was topically applied to the test subject's hip and covered by Glad's Press-N-Seal™ saran wrap for about 12 hours after the breaker bar was dropped. There was no control for pressure. The bruise that developed was rated a 10 on a scale from 0 to 10, increasing in severity.

Example 14

25% Water UV Hydrogel Alone (Pre-Loaded); Rating 8, 6 (Full Drop)

The effectiveness of a 2×4 inch UV hydrogel pre-loaded with 25% HASA to treat trauma incurred by dropping a breaker bar onto the hip of human test subject was studied. The HASA hydrogel composition was synthesized by producing HASA by combining 50M Amica lactose/sucrose pellets to produce 0.02% *Arnica* pellets in water. This HASA was then combined with a hydro-gelling agent mixture supplied by R&D Medical products Inc. This mixture was subsequently cross-linked with UV radiation to produce a hydrogel that was about 25% by weight water. The UV crosslinking ramped up to 170° F. for a few seconds. The number assigned to the production lot was #0819C10 and #0819D10, respective to the bruise ratings. The 50M *Arnica* was manufactured by Washington Homeopathic Products, Inc.

Prior to incurring any trauma, the hydrogel film post-loaded with HASA was topically applied to the hip region of the test subject for about 10 minutes. Subsequently, a 3 lb, 1 inch diameter breaker bar was dropped through a 2 inch diameter, 30 inch long paper tube that was held perpendicular to the body of the human test subject and onto the test subject's hip. The UV hydrogel film post-loaded with 25% HASA was topically applied to the test subject's hip and covered by Glad's Press-N-Seal™ saran wrap for about 12 hours after the breaker bar was dropped. This experiment was performed on two different occasions and at two different locations on the hip region. There was no control for pressure. The bruises that developed were rated an 8 and a 6 on a scale from 0 to 10, increasing in severity. The mean rating is a 7.00.+−0.1.41.

Post-Loaded Hydrogel

Example 15

Second Skin Post-Loaded with CF&E 50M (Laid on Pellets); Rating: 7

The effectiveness of a 2×4 inch e-beam radiation cross-linked Second Skin Dressing™ hydrogel film (Spenco) post-loaded with HASA to treat a trauma incurred by dropping a breaker bar onto the hip of human test subject was studied. The Second Skin Dressing™ hydrogel film post-loaded with HASA was produced by laying the hydrogel film on 1 gram of powdered 50M *Arnica, Ruta*, and *Ledum* lactose/sucrose pellets for 10 minutes. The resultant hydrogel film was then transferred on to a plate where it set for about 1 day. The homeopathic remedies were manufactured by Washington Homeopathic Products, Inc.

A 3 lb, 1 inch diameter breaker bar was dropped through a 2 inch diameter, 20 inch long paper tube that was held perpendicular to the body of the human test subject and onto the test subject's hip. The Second Skin Dressing™ hydrogel film post-loaded with HASA was topically applied to the test subject's hip and covered by Glad's Press-N-Seal™. saran wrap for about 17 hours after the breaker bar was dropped. There was no control for pressure. The bruise that developed was rated a 7 on a scale from 0 to 10, increasing in severity.

Example 16

Second Skin Soaked in CF&E 50M for 10 Mins and Applied 9 Weeks Later; Rating: 5

The effectiveness of a 2×4 inch e-beam radiation cross-linked Second Skin Dressing™ hydrogel film (produced by Spenco) post-loaded with HASA to treat a trauma incurred by dropping a breaker bar onto the hip of human test subject was studied. The HASA was synthesized by combining 1 gram of 50M *Arnica, Ruta*, and *Ledum* lactose/sucrose pellets per 8 ounces of water. Next, the Second Skin Dressing™ hydrogel film was post-loaded with HASA via soaking for 10 minutes. The resultant hydrogel film was then transferred on to a plastic bag where it set for about 9 weeks.

The homeopathic remedies were manufactured by Washington Homeopathic Products, Inc.

Prior to incurring any trauma, the Second Skin Dressing™ hydrogel film post-loaded with HASA was topically applied to the hip region of the test subject for about 30 minutes. Subsequently, a 3 lb, 1 inch diameter breaker bar was dropped through a 2 inch diameter, 20 inch long paper tube that was held perpendicular to the body of the human test subject and onto the test subject's hip. The Second Skin Dressing™ hydrogel film post-loaded with HASA was again topically applied to the test subject's hip and covered by Glad's Press-N-Seal™ saran wrap for the next 15 hours. No pressure was applied. The bruise that developed was rated a 5 on a scale from 0 to 10, increasing in severity.

Example 17

E-Beam Hydrogel Dipped in *Arnica* 50M; Rating: 5

The effectiveness of a 2×4 inch e-beam radiation cross-linked Second Skin Dressing™ hydrogel film (produced by Spenco) post-loaded with HASA to treat a trauma incurred by dropping a breaker bar onto the hip of human test subject was studied. The HASA was synthesized by combining 1 gram of 50M *Arnica* lactose/sucrose pellets per 8 ounces of water. Next, the Second Skin Dressing™ hydrogel film was post-loaded with HASA via dipping. The 50M *Arnica* was manufactured by Boiron®.

A 3 lb, 1 inch diameter breaker bar was dropped through a 2 inch diameter, 20 inch long paper tube that was held perpendicular to the body of the human test subject and onto the test subject's hip. The Second Skin Dressing™ hydrogel film post-loaded with HASA was again topically applied to the test subject's hip and covered by Glad's Press-N-Seal™ saran wrap. There was no control for pressure. No photographs were taken of this bruise; however the log book referenced a large, purple bruise developed. Based upon our rating scale, the rating would have been at least a 5.

Example 18

E-Beam Hydrogel Soaked in *Arnica* 50M for 20 Mins; Rating: 5

The effectiveness of a 2×4 inch e-beam radiation cross-linked Second Skin Dressing™ hydrogel film post-loaded with HASA to treat a trauma incurred by dropping a breaker bar onto the hip of human test subject was studied. The HASA was synthesized by combining 1 gram of 50M *Arnica* lactose/sucrose pellets per 8 ounces of water. Next, the Second Skin Dressing™ hydrogel film was post-loaded with HASA via soaking for 20 minutes. The 50M *Arnica* was manufacture by Boiron®.

A 3 lb, 1 inch diameter breaker bar was dropped through a 2 inch diameter, 20 inch long paper tube that was held perpendicular to the body of the human test subject and onto the test subject's hip. The Second Skin Dressing™ hydrogel film post-loaded with HASA was again topically applied to the test subject's hip and covered by Glad's Press-N-Seal™ saran wrap. There was no control for pressure. No photographs were taken of this bruise; however the log book referenced a large, purple bruise developed. Based upon our rating scale, the rating would have been at least a 5.

Example 19

90% Water UV Hydrogel *Arnica* (Post-Load Dip). Rating: 10 (Full Drop)

The effectiveness of a 2×4 inch 90% Water UV hydrogel post-loaded with HASA to treat trauma incurred by dropping a breaker bar onto the hip of human test subject was studied. A 90% water UV pre-loaded hydrogel, production described in example 14, was used. The number assigned to the production lot was #0819B10 and it was produced by R&D Medical. The HASA was synthesized by placing 1 gram of 50M *Arnica* lactose/sucrose pellets per 8 ounces of water. The 90% water UV hydrogel was post-loaded with HASA via dipping it in the 50M HASA *Arnica*.

Prior to incurring any trauma, the hydrogel film post-loaded with HASA was topically applied to the hip region of the test subject for about 10 minutes. Subsequently, a 3 lb, 1 inch diameter breaker bar was dropped through a 2 inch diameter, 30 inch long paper tube that was held perpendicular to the body of the human test subject and onto the test subject's hip. The 90% water UV hydrogel film post-loaded with HASA was topically applied to the test subject's hip and covered by Glad's Press-N-Seal™ saran wrap for about 12 hours after the breaker bar was dropped. There was no control for pressure. The bruise that developed was rated a 10 on a scale from 0 to 10, increasing in severity.

Placebo

Example 20

Second Skin and Polyurethane Placebo; Rating: 8, 2, 7, 5 (Half Drop)

The effectiveness of a 2×4 inch e-beam radiation cross-linked Second Skin Dressing™ hydrogel film or a polyurethane sponge soaked in water to treat a trauma incurred by dropping a breaker bar onto the hip of human test subject was studied. No HASA was added to the Second Skin Dressing™ hydrogel film or polyurethane sponge.

Prior to incurring any trauma, the Second Skin Dressing™ hydrogel film or the polyurethane sponge soaked in water was topically applied to the hip region of the test subject for approximately 10 minutes. Subsequently, a 3 lb, 1 inch diameter breaker bar was dropped through a 2 inch diameter, 20 inch long paper tube that was held perpendicular to the body of the human test subject and onto the test subject's hip. The Second Skin Dressing™ hydrogel film or polyurethane sponge soaked in water was again topically applied to the test subject's hip and covered using Glad's Press-N-Seal™ saran wrap for about 12 hours after the breaker bar was dropped. This experiment was performed on four different occasions and at four locations on the hip region of the test subject. There was no control for pressure. The bruises that developed were rated an 8, 2, 7, and 5 on a scale from 0 to 10, increasing in severity. The mean rating is a 5.50.+−0.2.64.

Example 21

Second Skin Placebo; Rating 6, 5 (Full Drop)

The effectiveness of a 2×4 inch e-beam radiation cross-linked Second Skin Dressing™ hydrogel (purchased from AquaMed Technologies, Inc., Langhorne, Pa.) film to treat a trauma incurred by dropping a breaker bar onto the hip of human test subject was studied. No HASA was added to the Second Skin Dressing™ hydrogel film.

Prior to incurring any trauma, the Second Skin Dressing™ hydrogel film was topically applied to the hip region of the test subject for approximately 10 minutes. Subsequently, a 3 lb, 1 inch diameter breaker bar was dropped through a 2 inch diameter, 30 inch long paper tube that was held perpendicular to the body of the human test subject and onto the test subject's hip. The Second Skin Dressing™ hydrogel film was again topically applied to the test subject's hip and covered using Glad's Press-N-Seal™ saran wrap for about 12 hours after the breaker bar was dropped. This experiment was performed on two different occasions and at two locations on the hip region of the test subject. There was no control for pressure. The bruises that developed were rated a 6 and a 5 on a scale from 0 to 10, increasing in severity. The mean rating is a 5.50.+−0.0.71

No Treatment

Example 22

No TX; Rating: 9 (Full Drop)

The effectiveness of not applying treatment to trauma incurred by dropping a breaker bar onto the hip of human test subject was studied. No HASA was used.

A 3 lb, 1 inch diameter breaker bar was dropped through a 2 inch diameter, 30 inch long paper tube that was held perpendicular to the body of the human test subject and onto the test subject's hip. Nothing was topically applied to the hip region. There was no control for pressure. The bruise that developed was rated a 9 on a scale from 0 to 10, increasing in severity.

Paper Towel & Water—1 hr

Example 23

Frozen & Melted CF&E 50M; Rating: 3

The effectiveness of HASA applied with a paper towel to treat trauma incurred by dropping a breaker bar onto the hip of human test subject was studied. HASA was synthesized by combining 1 gram of 50M *Arnica, Ruta,* and *Ledum* lactose/sucrose pellets per 8 ounces of water, and stirred vigorously. Next, the HASA was frozen and then melted before application. The homeopathic remedies were manufactured by Washington Homeopathic Products, Inc.

Prior to incurring any trauma, a 2×4 inch paper towel soaked with HASA was topically applied to the hip region of the test subject for approximately 20 minutes. Subsequently, a 3 lb, 1 inch diameter breaker bar was dropped through a 2 inch diameter, 20 inch long paper tube that was held perpendicular to the body of the human test subject and onto the test subject's hip. The paper towel soaked in HASA was again topically applied to the test subject's hip and covered by Glad's Press-N-Sea™ saran wrap for the next 15 hours. No pressure was applied. The bruise that developed was rated a 3 on a scale from 0 to 10, increasing in severity.

Example 24

Arnica 50 M Amorphous Hydrogel; Rating: 1

The effectiveness of a HASA hydrogel composition to treat trauma incurred by dropping a breaker bar onto the hip of human test subject was studied. The HASA hydrogel composition was synthesized as a film by producing HASA by ratio using 8.2 grams of medicated 50M *Arnica,* 50M *Ledum* and 50M *Ruta* lactose/sucrose pellets per 1 gallon of water and stirred. 97.8% HASA was then combined with a hydrophilic polymer mixture to form a hydrogel supplied by Marble Medical Inc. The gelling occurred at room temperature. The resultant HASA hydrogel composition comprised about 97.8% by weight water, all of which was from the HASA mixture. The number assigned to the production lot was #24961-00. The 50M Amica and 50M *Ledum* were manufactured by Washington Homeopathic Products Inc.

Prior to incurring any trauma, a 2×4 inch HASA hydrogel composition was topically applied to the hip region of the test subject for about 1 hour. Subsequently, a 3 lb, 1 inch diameter breaker bar was dropped through a 2 inch diameter, 20 inch long paper tube that was held perpendicular to the body of the human test subject and onto the test subject's hip. The HASA hydrogel composition was again topically applied to the test subject's hip and covered by Glad's Press-N-Seal™ saran wrap for about 16 hours after the breaker bar was dropped. No pressure was applied. The bruise that developed was rated a 1 on a scale from 0 to 10, increasing in severity.

Example 25

Amica 50 M and *Ledum* 50M Hydrogel; Rating: 3, 1, 0, 1, 0, and 1

The effectiveness of a HASA hydrogel composition to treat trauma incurred by dropping a breaker bar onto the hip of human test subject was studied. The HASA hydrogel composition was synthesized as a film by producing HASA by ratio using 8.2 grams of medicated 50M *Arnica* and 50M *Ledum* lactose/sucrose pellets per 1 gallon of water and stirred. 63% HASA was then combined with a hydrophilic polymer mixture supplied by Katecho Inc. This HASA and hydrophilic polymer mixture was subsequently cross-linked with UV curing at 1.3.+−0.0.1 J/cm$^2$. The resultant HASA hydrogel composition comprised about 72% by weight water. 63% of the total water content was from the HASA mixture. The numbers assigned to the production lots were X061011-16, X061011-14, X061011-15, X061011-15, X20111103-14 and X20111103-16 respective to the bruise ratings. The 50M *Arnica* and 50M *Ledum* were manufactured by Washington Homeopathic Products Inc.

Prior to incurring any trauma, a 2×4 inch HASA hydrogel composition was topically applied to the hip region of the test subject for about 1 hour. Subsequently, a 3 lb, 1 inch diameter breaker bar was dropped through a 2 inch diameter, 20 inch long paper tube that was held perpendicular to the body of the human test subject and onto the test subject's hip. The HASA hydrogel composition was again topically applied to the test subject's hip and covered by Glad's Press-N-Seal™ saran wrap for about 15 hours after the breaker bar was dropped. No pressure was applied. The bruises that developed were rated a 3, 1, 0, 1, 0 and 1 on a scale from 0 to 10, increasing in severity.

Example 26

*Arnica* 50 M and *Ledum* 50M Hydrogel; Rating: 5, 8

The effectiveness of a HASA hydrogel composition to treat trauma incurred by dropping a breaker bar onto the hip of human test subject was studied. The HASA hydrogel composition was synthesized as a film by producing HASA by ratio using 8.2 grams of medicated 50M *Arnica* and 50M *Ledum* lactose/sucrose pellets per 1 gallon of water and stirred. 63% HASA was then combined with a hydrophilic polymer mixture supplied by Katecho Inc. This HASA and hydrophilic polymer mixture was subsequently cross-linked with UV curing at 1.3.+−0.0.1 J/cm$^2$ and a temperature rise to 135° F.-140° F. The resultant HASA hydrogel composition comprised about 72% by weight water. 63% of the total water content was from the HASA mixture. The number assigned to the production lot was #20111103-15 (the same lot was tested twice). The 50M *Arnica* and 50M *Ledum* were manufactured by Washington Homeopathic Products Inc.

Prior to incurring any trauma, a 4×4 inch HASA hydrogel composition was topically applied to the hip region of the test subject for about 1 hour. Subsequently, a 3 lb, 1 inch diameter breaker bar was dropped through a 2 inch diameter, 20 inch long paper tube that was held perpendicular to the body of the human test subject and onto the test subject's hip. The HASA hydrogel composition was again topically applied to the test subject's hip and covered by Glad's Press-N-Seal™ saran wrap for about 15 hours after the breaker bar was dropped. No pressure was applied. The bruises that developed were rated a 5 and 8 on a scale from 0 to 10, increasing in severity.

Example 27

Polyurethane and CF&E (Half); Rating: 5

The effectiveness of a polyurethane sponge to treat a trauma incurred by dropping a breaker bar onto the hip of human test subject was studied. The HASA was synthesized by combining 1 gram of 50M *Arnica*, *Ruta*, and *Ledum* lactose/sucrose pellets per 8 ounces of water. A 2×4 quarter-inch polyurethane sponge was soaked in the HASA mixture for about 1 minute.

Prior to incurring any trauma, the wet polyurethane sponge was topically applied to the hip region of the test subject for approximately 2 minutes. Subsequently, a 3 lb, 1 inch diameter breaker bar was dropped through a 2 inch diameter, 20 inch long paper tube that was held perpendicular to the body of the human test subject and onto the test subject's hip. The polyurethane sponge soaked in HASA mixture was again topically applied to the test subject's hip and covered using Glad's Press-N-Seal™ saran wrap for about 16 hours after the breaker bar was dropped. No pressure was applied. The bruise that developed was rated a 5 on a scale from 0 to 10, increasing in severity.

Example 28

*Arnica* 50M and *Ledum* 50M PT&W; Rating: 0

The effectiveness of HASA applied with a paper towel to treat trauma incurred by dropping a breaker bar onto the hip of human test subject was studied. HASA was synthesized by combining 1 gram of 50M *Arnica* and 50M *Ledum* lactose/sucrose pellets per 8 ounces of water. The homeopathic remedies were manufactured by Washington Homeopathic Products, Inc.

Prior to incurring any trauma, a 2×4 inch paper towel soaked with HASA was topically applied to the hip region of the test subject. Subsequently, a 3 lb, 1 inch diameter breaker bar was dropped through a 2 inch diameter, 20 inch long paper tube that was held perpendicular to the body of the human test subject and onto the test subject's hip. The paper towel soaked in HASA was again topically applied to the test subject's hip and covered by Glad's Press-N-Seal™ saran wrap. No pressure was applied. The bruise that developed was rated a 0 on a scale from 0 to 10, increasing in severity.

Example 29

50% *Calendula* gel and 50% 50M *Arnica* Water Mixture; Rating: 1

The effectiveness of a mixture of *Calendula* gel and 50M Arnica Water mixture to treat a trauma incurred by dropping a breaker bar onto the inner thigh of human test subject was studied. The HASA was synthesized by combining 1 gram of 50M Arnica lactose/sucrose pellets per 8 ounces of water. The Arnica 50M was manufactured by Boiron. 26 g of this mixture was then combined with 26 g of *Calendula* gel to produce a mixture that contains 50% HASA mixture and 50% *Calendula* gel by weight. *Calendula* is a remedy that does not affect bruising. The *Calendula* gel, manufactured by Boiron, consists of caprylyl glycol, carbomer, dimethicone copolyol, EDTA disodium, purified water, sodium hydroxide, sorbic acid, 1,2-hexanediol and *Calendula* officinalis 1×. A 3"×3" gauze was coated with the mixture.

Prior to incurring any trauma, the coated gauze was topically applied to the thigh region of the test subject for approximately 1 hour. Subsequently, a 3 lb, 1 inch diameter breaker bar was dropped through a 2 inch diameter, 20 inch long paper tube that was held perpendicular to the body of the human test subject and onto the test subject's inner thigh. The gauze soaked in HASA mixture was again topically applied to the test subject's inner thigh and covered using Tegaderm and Glad's Press-N-Seal™ saran wrap for about 15 hours after the breaker bar was dropped. No pressure was applied. The gauze was still moist upon removal. The bruise that developed was rated a 1 on a scale from 0 to 10, increasing in severity.

Example 30

90% *Calendula* Gel and 10% 50M *Arnica* Water Mixture; Rating: 7

The effectiveness of a mixture of *Calendula* gel and 50M Arnica Water mixture to treat a trauma incurred by dropping a breaker bar onto the inner thigh of human test subject was studied. The HASA was synthesized by combining 1 gram of 50M Arnica lactose/sucrose pellets per 8 ounces of water. The Arnica 50M was manufactured by Boiron. 2.78 g of this mixture was then combined with 25 g of *Calendula* gel to produce a mixture that contains 10% HASA mixture and 90% *Calendula* gel by weight. *Calendula* is a remedy that does not affect bruising. The *Calendula* gel, manufactured by Boiron, consists of caprylyl glycol, carbomer, dimethicone copolyol, EDTA disodium, purified water, sodium hydroxide, sorbic acid, 1,2-hexanediol and *Calendula* officinalis 1×. A 3"×3" gauze was coated with the mixture.

Prior to incurring any trauma, the coated gauze was topically applied to the thigh region of the test subject for approximately 1 hour. Subsequently, a 3 lb, 1 inch diameter breaker bar was dropped through a 2 inch diameter, 20 inch long paper tube that was held perpendicular to the body of the human test subject and onto the test subject's inner thigh. The gauze soaked in HASA mixture was again topically applied to the test subject's inner thigh and covered using Tegaderm and Glad's Press-N-Seal™ saran wrap for about 15 hours after the breaker bar was dropped. No pressure was applied. The gauze was still moist upon removal. The bruise that developed was rated a 7 on a scale from 0 to 10, increasing in severity.

Example 31

80% *Calendula* gel and 20% 50M *Arnica* Water Mixture; Rating: 7

The effectiveness of a mixture of *Calendula* gel and 50M Arnica Water mixture to treat a trauma incurred by dropping a breaker bar onto the inner thigh of human test subject was studied. The HASA was synthesized by combining 1 gram of 50M Arnica lactose/sucrose pellets per 8 ounces of water. The Arnica 50M was manufactured by Boiron. 2 g of this mixture was then combined with 8 g of *Calendula* gel to produce a mixture that contains 20% HASA mixture and 80% *Calendula* gel by weight. *Calendula* is a remedy that does not affect bruising. The *Calendula* gel, manufactured by Boiron, consists of caprylyl glycol, carbomer, dimethicone copolyol, EDTA disodium, purified water, sodium hydroxide, sorbic acid, 1,2-hexanediol and *Calendula* officinalis 1x. A 3"×3" gauze was coated with the mixture.

Prior to incurring any trauma, the coated gauze was topically applied to the thigh region of the test subject for approximately 1 hour. Subsequently, a 3 lb, 1 inch diameter breaker bar was dropped through a 2 inch diameter, 20 inch long paper tube that was held perpendicular to the body of the human test subject and onto the test subject's inner thigh. The gauze soaked in HASA mixture was again topically applied to the test subject's inner thigh and covered using Tegaderm and Glad's Press-N-Seal™ saran wrap for about 15 hours after the breaker bar was dropped. No pressure was applied. The gauze was still moist upon removal. The bruise that developed was rated a 7 on a scale from 0 to 10, increasing in severity.

Example 32

70% *Calendula* Gel and 30% 50M *Arnica* Water Mixture; Rating: 7

The effectiveness of a mixture of *Calendula* gel and 50M Arnica Water mixture to treat a trauma incurred by dropping a breaker bar onto the inner thigh of human test subject was studied. The HASA was synthesized by combining 1 gram of 50M Arnica lactose/sucrose pellets per 8 ounces of water. The Arnica 50M was manufactured by Boiron. 3 g of this mixture was then combined with 7 g of *Calendula* gel to produce a mixture that contains 30% HASA mixture and 70% *Calendula* gel by weight. *Calendula* is a remedy that does not affect bruising. The *Calendula* gel, manufactured by Boiron, consists of caprylyl glycol, carbomer, dimethicone copolyol, EDTA disodium, purified water, sodium hydroxide, sorbic acid, 1,2-hexanediol and *Calendula* officinalis 1×A 3"×3" gauze was coated with the mixture.

Prior to incurring any trauma, the coated gauze was topically applied to the thigh region of the test subject for approximately 1 hour. Subsequently, a 3 lb, 1 inch diameter breaker bar was dropped through a 2 inch diameter, 20 inch long paper tube that was held perpendicular to the body of the human test subject and onto the test subject's inner thigh. The gauze soaked in HASA mixture was again topically applied to the test subject's inner thigh and covered using Tegaderm and Glad's Press-N-Seal™ saran wrap for about 15 hours after the breaker bar was dropped. No pressure was applied. The gauze was still moist upon removal. The bruise that developed was rated a 7 on a scale from 0 to 10, increasing in severity.

Example 33

60% *Calendula* Gel and 40% 50M *Arnica* Water Mixture; Rating: 7

The effectiveness of a mixture of *Calendula* gel and 50M Arnica Water mixture to treat a trauma incurred by dropping a breaker bar onto the inner thigh of human test subject was studied. The HASA was synthesized by combining 1 gram of 50M Arnica lactose/sucrose pellets per 8 ounces of water. The Arnica 50M was manufactured by Boiron. 11 g of this mixture was then combined with 17 g of *Calendula* gel to produce a mixture that contains 40% HASA mixture and 60% *Calendula* gel by weight. *Calendula* is a remedy that does not affect bruising. The *Calendula* gel, manufactured by Boiron, consists of caprylyl glycol, carbomer, dimethicone copolyol, EDTA disodium, purified water, sodium hydroxide, sorbic acid, 1,2-hexanediol and *Calendula* officinalis 1x. A 3"×3" gauze was coated with the mixture.

Prior to incurring any trauma, the coated gauze was topically applied to the thigh region of the test subject for approximately 1 hour. Subsequently, a 3 lb, 1 inch diameter breaker bar was dropped through a 2 inch diameter, 20 inch long paper tube that was held perpendicular to the body of the human test subject and onto the test subject's inner thigh. The gauze soaked in HASA mixture was again topically applied to the test subject's inner thigh and covered using Tegaderm and Glad's Press-N-Seal™ saran wrap for about 15 hours after the breaker bar was dropped. No pressure was applied. The gauze was still moist upon removal. The bruise that developed was rated a 7 on a scale from 0 to 10, increasing in severity.

Example 34

Arnica 50 M and *Ledum* 50M Hydrogel; Rating: 0

The effectiveness of a HASA hydrogel composition to treat trauma incurred by dropping a breaker bar onto the hip of human test subject was studied. The HASA hydrogel composition was synthesized as a film by producing HASA by ratio using 8.2 grams of medicated 50M *Arnica* and 50M *Ledum* lactose/sucrose pellets per 1 gallon of water and stirred. 63% HASA was then combined with a hydrophilic polymer mixture supplied by Katecho Inc. This HASA and hydrophilic polymer mixture was subsequently cross-linked with UV curing at $1.3.+-0.0.1$ J/cm$^2$. The resultant HASA hydrogel composition comprised about 72% by weight water. 63% of the total water content was from the HASA mixture. The number assigned to this production lot was #051611-2. The 50M *Arnica* and 50M *Ledum* were manufactured by Washington Homeopathic Products Inc.

Prior to incurring any trauma, a 2×4 inch HASA hydrogel composition was topically applied to the hip region of the test subject for about 1 hour. Subsequently, a 3 lb, 1 inch diameter breaker bar was dropped through a 2 inch diameter, 20 inch long paper tube that was held perpendicular to the body of the human test subject and onto the test subject's hip. The HASA hydrogel composition was again topically applied to the test subject's hip and covered by Glad's Press-N-Seal™ saran wrap for about 15 hours after the breaker bar was dropped. No pressure was applied. The bruises that developed were rated 0 on a scale from 0 to 10, increasing in severity.

Example 35

A topical HASA application of 6 C ($10^{-12}$) of *naturam sulphuricum* and *thuja* was topically applied for 6 hours at night below the eye to treat a chalazon. Then next morning the swelling associated was more than 50% reduced and the chalazon was significantly smaller.

The invention claimed is:

1. A method of producing a hydrophilic homeopathic gel matrix, the method comprising the steps of: (a) combining diluted aqueous calendula composition comprising homeopathic calendula and uninhibited water at a calendula-to-water ratio of no more than 0.000001 with at least one hydrophilic gelling agent to produce a solution comprising the hydrophilic gelling agent and the diluted aqueous calendula composition; and (b) forming the hydrophilic gel matrix by crosslinking or diluted aqueous calendula composition.

2. The method of claim 1, wherein the diluted aqueous calendula composition comprises homeopathic calendula and uninhibited water at a ratio of no more than 0.00000001.

3. The method of claim 1, wherein the diluted aqueous calendula composition comprises homeopathic calendula and uninhibited water at a ratio of no more than 0.00000000001.

4. The method of claim 1, wherein the hydrophilic homeopathic gel matrix comprises at least 50% by weight of the diluted aqueous calendula solution.

5. The method of claim 1, further comprising forming the hydrophilic homeopathic gel matrix into a sheet.

6. The method of claim 5, further comprising affixing an impermeable layer to a first major surface of the gel sheet.

7. The method of claim 6, further comprising affixing a permeable layer to a second major surface of the gel sheet opposite the first major surface.

8. The method of claim 1, wherein the hydrophilic homeopathic-gel matrix is in a flowable form.

9. The method of claim 1, wherein the crosslinking is induced by at least one of temperature, pressure, change in pH, radiation, and/or a chemical crosslinking agent.

10. The method of claim 9, wherein the radiation is ultraviolet light, gamma radiation, or electron beam radiation.

11. The method of claim 1, wherein the hydrophilic gelling agent comprises one or more cationic, anionic, or nonionic polar polymers.

12. The method of claim 1, wherein the hydrophilic gelling agent comprises polyethylene oxide, polypropylene oxide, polyacrylamide, polyvinyl alcohol, polyvinylpyrrolidone, polyacrylonitrile, or combinations or co-polymers thereof.

13. The method of claim 1, wherein the hydrophilic gelling agent comprises polyacrylic acid, polysulfonic acid, or a salt of either thereof.

14. The method of claim 1, wherein the hydrophilic gelling agent comprises an acrylic, an amine-functional polymer, an ether, a styrene, a polystyrenesulfonate, a vinyl acid, a vinyl alcohol, or polyvinylpyrrolidone.

15. The method of claim 1, wherein the hydrophilic gelling agent comprises an acrylic, an acrylamide or an acrylate.

16. The method of claim 1, wherein the hydrophilic gelling agent comprises poly(acrylic acid), a maleic anhydride copolymer, methacrylate, or ethacrylate.

17. The method of claim 1, wherein the hydrophilic gelling agent comprises an alkali metal salt of a polyacrylic acid, a polyacrylamide, a polyvinyl alcohol, a polyacrylate, a polyacrylamide, a polyvinylpyridine, a poly(vinyl alcohol), a polyion complex, hydrolyzed acrylonitrile grafted starch, acrylic acid grafted starch, or an isobutylene maleic anhydride copolymer.

18. The method of claim 1, wherein the hydrophilic gelling agent comprises carboxymethylcellulose, hyaluronic acid, dextran, dextran sulfate, heparin, chondroitin sulfate, gelatin, collagen, albumin, cellulose, starch, chitin, a chitosan, a lignin, agar, keratin, alginic acid, silk, wool, or natural rubber.

19. The method of claim 1, wherein the hydrophilic homeopathic gel matrix comprises at least 41% by weight of the diluted aqueous calendula solution, and wherein the matrix is sufficiently cross-linked to inhibit total absorption of the calendula solution when the calendula solution is placed on the skin of a user for a period of at least 48 hours.

* * * * *